(12) United States Patent
Chee

(10) Patent No.: US 9,783,847 B2
(45) Date of Patent: Oct. 10, 2017

(54) NUCLEIC ACID CONSTRUCTS AND METHODS OF USE

(71) Applicant: Prognosys Biosciences, Inc., San Diego, CA (US)

(72) Inventor: Mark S. Chee, Encinitas, CA (US)

(73) Assignee: PROGNOSYS BIOSCIENCES, INC., San Diego, CA (US)

( * ) Notice: Subject to any disclaimer, the term of this patent is extended or adjusted under 35 U.S.C. 154(b) by 0 days.

(21) Appl. No.: 14/723,332

(22) Filed: May 27, 2015

(65) Prior Publication Data

US 2016/0024576 A1 Jan. 28, 2016

Related U.S. Application Data

(62) Division of application No. 13/266,568, filed as application No. PCT/US2010/033064 on Apr. 29, 2010, now Pat. No. 9,085,798.

(60) Provisional application No. 61/174,442, filed on Apr. 30, 2009.

(51) Int. Cl.
*C12Q 1/68* (2006.01)

(52) U.S. Cl.
CPC ......... *C12Q 1/6869* (2013.01); *C12Q 1/6806* (2013.01); *C12Q 1/6809* (2013.01); *C12Q 1/6827* (2013.01); *C12Q 1/6834* (2013.01); *C12Q 1/6874* (2013.01); *C12Q 1/6876* (2013.01)

(58) Field of Classification Search
None
See application file for complete search history.

(56) References Cited

U.S. PATENT DOCUMENTS

| | | |
|---|---|---|
| 5,002,882 A | 3/1991 | Lunnen et al. |
| 5,308,751 A | 5/1994 | Ohkawa et al. |
| 5,512,439 A | 4/1996 | Hornes et al. |
| 6,013,440 A | 1/2000 | Lipshutz et al. |
| 6,143,496 A | 11/2000 | Brown et al. |
| 6,153,389 A | 11/2000 | Haarer et al. |
| 6,210,894 B1 | 4/2001 | Brennan |
| 6,258,558 B1 | 7/2001 | Szostak et al. |
| 6,261,804 B1 | 7/2001 | Szostak et al. |
| 6,281,804 B1 | 8/2001 | Haller et al. |
| 6,344,316 B1 | 2/2002 | Lockhart et al. |
| 6,404,907 B1 | 6/2002 | Gilchrist et al. |
| 6,416,950 B1 | 7/2002 | Lohse et al. |
| 6,485,982 B1 | 11/2002 | Charlton |
| 6,518,018 B1 | 2/2003 | Szostak et al. |
| 6,579,695 B1 | 6/2003 | Lambalot et al. |
| 6,632,641 B1 | 10/2003 | Brennan et al. |
| 6,773,886 B2 | 8/2004 | Kaufman et al. |
| 6,800,453 B2 | 10/2004 | Labaer et al. |
| 6,833,246 B2 | 12/2004 | Balasubramanian |
| 6,878,515 B1 | 4/2005 | Landegren |
| 7,118,883 B2 | 10/2006 | Inoue et al. |
| 7,192,735 B2 | 3/2007 | Lambalot et al. |
| 7,229,769 B2 | 6/2007 | Kozlov et al. |
| 7,264,929 B2 | 9/2007 | Rothberg et al. |
| 7,270,950 B2 | 9/2007 | Szostak et al. |
| 7,378,242 B2 | 5/2008 | Hurt |
| 7,393,665 B2 | 7/2008 | Brenner |
| 7,407,757 B2 | 8/2008 | Brenner |
| 7,537,897 B2 | 5/2009 | Brenner et al. |
| 7,544,473 B2 | 6/2009 | Brenner |
| 7,579,153 B2 | 8/2009 | Brenner et al. |
| 7,635,566 B2 | 12/2009 | Brenner |
| 7,666,612 B2 | 2/2010 | Johnsson et al. |
| 7,674,752 B2 | 3/2010 | He et al. |
| 7,754,429 B2 | 7/2010 | Rigatti et al. |
| 7,858,321 B2 | 12/2010 | Glezer et al. |
| 8,148,068 B2 | 4/2012 | Brenner |
| 8,207,093 B2 | 6/2012 | Szostak et al. |
| 8,337,851 B2 | 12/2012 | Aukerman et al. |
| 8,343,500 B2 | 1/2013 | Wraith et al. |
| 8,383,338 B2 | 2/2013 | Kitzman et al. |
| 8,481,292 B2 | 7/2013 | Casbon et al. |
| RE44,596 E | 11/2013 | Stroun et al. |
| 8,741,606 B2 | 6/2014 | Casbon et al. |
| 8,835,358 B2 | 9/2014 | Fodor et al. |
| 8,865,410 B2 | 10/2014 | Shendure et al. |
| 9,085,798 B2 | 7/2015 | Chee |
| 9,121,069 B2 | 9/2015 | Lo et al. |

(Continued)

FOREIGN PATENT DOCUMENTS

| | | |
|---|---|---|
| DE | 102008025656 A1 | 12/2009 |
| EP | 1712623 A2 | 10/2006 |

(Continued)

OTHER PUBLICATIONS

Advisory Action for U.S. Appl. No. 13/080,616, dated Mar. 17, 2015, 2 pages.
Advisory Action for U.S. Appl. No. 13/442,637, dated Apr. 1, 2013.
Anderson et al., Microarrayed Compound Screening to Identify Activators and Inhibitors of AMP-Activated Protein Kinase, J. of Biomolecular Screening (2004) 9:112.
Angenendt et al., Cell-free expression and functional assay in a nanowell chip format. Analytical Chemistry (2004) 76(7):1844-49.
Angenendt et al., Generation of High Density Protein Microarrays by Cell-free in Situ Expression of Unpurified PCR Products, Molecular and Cellular Proteomics (2006) Ch. 5.9, pp. 1658-1666.
Atkinson, Overview of Translation: Lecture Manuscript, U of Texas (2000) pp. 6.1-6.8.

(Continued)

*Primary Examiner* — Nancy Treptow
(74) *Attorney, Agent, or Firm* — Wilson Sonsini Goodrich & Rosati

(57) ABSTRACT

The present invention provides oligonucleotide constructs, sets of such oligonucleotide constructs, and methods of using such oligonucleotide constructs to provide validated sequences or sets of validated sequences corresponding to desired ROIs. Such validated ROIs and constructs containing these have a wide variety of uses, including in synthetic biology, quantitative nucleic acid analysis, polymorphism and/or mutation screening, and the like.

30 Claims, 13 Drawing Sheets

(56) References Cited

U.S. PATENT DOCUMENTS

| | | |
|---|---|---|
| 9,194,001 B2 | 11/2015 | Brenner |
| 9,290,808 B2 | 3/2016 | Fodor et al. |
| 9,290,809 B2 | 3/2016 | Fodor et al. |
| 9,340,830 B2 | 5/2016 | Downing et al. |
| 9,404,156 B2 | 8/2016 | Hicks et al. |
| 9,574,230 B2 | 2/2017 | Van Eijk et al. |
| 2003/0087232 A1 | 5/2003 | Christians et al. |
| 2003/0096323 A1 | 5/2003 | James et al. |
| 2003/0113713 A1 | 6/2003 | Glezer et al. |
| 2003/0138879 A1 | 7/2003 | Lambalot et al. |
| 2003/0162216 A1 | 8/2003 | Gold et al. |
| 2003/0224419 A1 | 12/2003 | Corcoran et al. |
| 2003/0232382 A1 | 12/2003 | Brennan et al. |
| 2003/0235852 A1 | 12/2003 | Roberts et al. |
| 2005/0019776 A1 | 1/2005 | Callow et al. |
| 2005/0026188 A1 | 2/2005 | Van Kessel et al. |
| 2005/0048580 A1 | 3/2005 | Labaer et al. |
| 2005/0164292 A1 | 7/2005 | Farooqui et al. |
| 2005/0255548 A1 | 11/2005 | Lipovsek et al. |
| 2005/0260653 A1 | 11/2005 | Labaer et al. |
| 2006/0003394 A1 | 1/2006 | Song |
| 2006/0046313 A1 | 3/2006 | Roth et al. |
| 2006/0134669 A1 | 6/2006 | Casasanta, III et al. |
| 2006/0216721 A1 | 9/2006 | Kozlov et al. |
| 2006/0216775 A1 | 9/2006 | Burkart et al. |
| 2006/0275799 A1 | 12/2006 | Banerjee et al. |
| 2007/0014810 A1 | 1/2007 | Baker et al. |
| 2007/0020625 A1 | 1/2007 | Duchaud et al. |
| 2007/0020669 A1 | 1/2007 | Ericsson |
| 2007/0026430 A1 | 2/2007 | Andersen et al. |
| 2007/0172873 A1 | 7/2007 | Brenner et al. |
| 2008/0071071 A1 | 3/2008 | LaBaer et al. |
| 2008/0108804 A1 | 5/2008 | Hayashizaki et al. |
| 2008/0220981 A1 | 9/2008 | McGregor |
| 2008/0261204 A1 | 10/2008 | Lexow |
| 2008/0293591 A1 | 11/2008 | Taussig et al. |
| 2008/0312103 A1 | 12/2008 | Nemoto et al. |
| 2009/0006002 A1 | 1/2009 | Honisch et al. |
| 2009/0099041 A1 | 4/2009 | Church et al. |
| 2009/0105959 A1 | 4/2009 | Braverman et al. |
| 2009/0215633 A1 | 8/2009 | Van Eijk et al. |
| 2009/0280487 A1 | 11/2009 | Hung et al. |
| 2009/0291854 A1 | 11/2009 | Wiesinger-Mayr et al. |
| 2010/0069263 A1 | 3/2010 | Shendure et al. |
| 2010/0099103 A1 | 4/2010 | Hsieh et al. |
| 2010/0113302 A1 | 5/2010 | Williams |
| 2010/0173384 A1 | 7/2010 | Johnsson et al. |
| 2010/0184614 A1 | 7/2010 | Ye et al. |
| 2010/0227329 A1 | 9/2010 | Cuppens |
| 2011/0245101 A1 | 10/2011 | Chee et al. |
| 2011/0245111 A1 | 10/2011 | Chee |
| 2012/0046175 A1 | 2/2012 | Rodesch et al. |
| 2012/0129248 A1 | 5/2012 | Chee et al. |
| 2012/0195810 A1 | 8/2012 | Cohen et al. |
| 2012/0258871 A1 | 10/2012 | Kozlov et al. |
| 2012/0270748 A1 | 10/2012 | Chee et al. |
| 2013/0096033 A1 | 4/2013 | Routenberg |
| 2013/0109595 A1 | 5/2013 | Routenberg |
| 2014/0065609 A1 | 3/2014 | Hicks et al. |
| 2014/0121118 A1 | 5/2014 | Warner |
| 2014/0155274 A1 | 6/2014 | Xie et al. |
| 2014/0227705 A1 | 8/2014 | Vogelstein et al. |
| 2014/0274731 A1 | 9/2014 | Raymond et al. |
| 2014/0296081 A1 | 10/2014 | Diehn et al. |
| 2015/0051085 A1 | 2/2015 | Vogelstein et al. |
| 2016/0003812 A1 | 1/2016 | Porreca et al. |

FOREIGN PATENT DOCUMENTS

| | | | |
|---|---|---|---|
| JP | 2014217381 A | | 11/2014 |
| WO | WO-9844151 A1 | | 10/1998 |
| WO | WO-0018957 A1 | | 4/2000 |
| WO | WO-03010176 A2 | | 2/2003 |
| WO | WO-2005026387 A1 | | 3/2005 |
| WO | WO-2005042759 A2 | | 5/2005 |
| WO | WO-2006084130 A2 | | 8/2006 |
| WO | WO-2007041689 A2 | | 4/2007 |
| WO | WO-2007060599 A1 | | 5/2007 |
| WO | WO2007/073171 | * | 6/2007 |
| WO | WO2007/076726 | * | 7/2007 |
| WO | WO-2007145612 A1 | | 12/2007 |
| WO | WO-2009032167 A1 | | 3/2009 |
| WO | WO-2009036525 A2 | | 3/2009 |
| WO | WO-2010019826 A1 | | 2/2010 |
| WO | WO-2010127186 A1 | | 11/2010 |
| WO | WO-2011014879 A2 | | 2/2011 |
| WO | WO-2011071943 A1 | | 6/2011 |
| WO | WO-2011127006 A1 | | 10/2011 |
| WO | WO-2011127099 A1 | | 10/2011 |
| WO | WO-2012139110 A2 | | 10/2012 |
| WO | WO-2012142213 A2 | | 10/2012 |
| WO | WO-2012148477 A1 | | 11/2012 |
| WO | WO-2013123442 A1 | | 8/2013 |
| WO | WO-2013138510 A1 | | 9/2013 |
| WO | WO-2013142389 A1 | | 9/2013 |
| WO | WO-2014210223 A1 | | 12/2014 |
| WO | WO-2014210225 A1 | | 12/2014 |

OTHER PUBLICATIONS

Bielas et al., Human cancers express a mutator phenotype. Proc. Natl. Acad. Sci. USA 103(48): 18238-18242 (2006).

Bielas et al., Quantification of random genomic mutations. Nat. Methods 2(4):285-290 (2005).

Blokzijl et al., Profiling protein expression and interactions: proximity ligation as a tool for personalized medicine. J Intern Med (2010) 268:232-245.

Bowtell, The genesis and evolution of high-grade serous ovarian cancer. Nat. Rev. Cancer (11 ):803-808 (2010).

Brandon et al., Mitochondrial mutations in cancer. Oncogene 25(34):4647-4662 (2006).

Brenner, S. et al. In vitro cloning of complex mixtures of DNA on microbeads: physical separation of differentially expressed cDNAs. Proc. Natl. Acad. Sci. USA 97, 1665-1670.

Burns, et al., Well-less, gel-permeation formats for ultra-HTS, DDT (2001) 6(12):S40-S47.

Carlson et al., Formylglycine-generating Enzyme, J. of Biological Chemistry (2008) 283(29):20117-125.

Cha and Tilly, Specificity, Efficiency and Fidelity of PCR, Genome Res., 3:518-29 (1993).

Chandra et al., Cell-free synthesis-based protein microarrays and their applications, Proteomics ePub, (2009) 5(6):717-30.

Chatterjee et al., Microarray System, PLoS One (2008) 3(9):e3265.

Chatterjee, et al., Mitochondrial DNA mutations in human cancer. Oncogene 25(34):4663-4674 (2006).

Cheng et al., Sensitive Detection of Small Molecules by Competitive D Immunomagnetic-Proximity Ligation Assay, Anal Chem (2012) 84:2129-2132.

Schmitt et al., Detection of ultra-rare mutations by next-generation sequencing, PNAS (2012) 109:14508-14523.

Communication Pursuant to Art. 94(3) EPC for EP 10747097.3-1405, dated Jul. 26. 2013.

Communication pursuant to Article 94(3) EPC for EP 11766613.1, dated Aug. 22, 2014, 4 pages.

Copeland et al., Mitochondrial DNA Alterations in Cancer. Cancer Invest. 20(4):557-569 (2002).

Darmanis et al., ProteinSeq: High-Performance Proteomic Analyses by Proximity Ligation and Next Generation Sequencing, PLoS One (2011) 6(9):e25583.

Ellington et al., Antibody-based protein multiplex platforms: technical and operational challenges, Clin Chem (2010) 56(2):186-193.

European Search Report for EP 11766613.1, dated Jan. 15, 2014, 6 pages.

Examination Report for European Patent Application No. EP 10836568.5, dated Mar. 12, 2014, pp. 1-3.

Examination Report issued in European Patent Application No. 10836568.5, dated Mar. 12, 2014, 3 pages.

Final Office Action for U.S. Appl. No. 13/080,616, dated Oct. 21, 2014.

(56) References Cited

OTHER PUBLICATIONS

Final Office Action for U.S. Appl. No. 13/442,637, dated Dec. 20, 2012.
Final Office Action for U.S. Appl. No. 13/514,045, dated Oct. 18, 2013.
First Examination Report for CN 201180017696.3, dated Oct. 18, 2013.
First Examination Report for EP 10836568.5-1403, dated Oct. 1, 2013.
First Office Action for CN 201080055351.2, dated Jul. 23, 2013.
Flanigon et al., Multiplex protein detection with DNA readout via mass spectrometry, N Biotechnol (2013) 30(2): 153-158.
Fredriksson et al., Multiplexed protein detection by proximity ligation for cancer detection, Nature Methods (2007) 4(4):327-29.
Fredriksson et al., Multiplexed proximity ligation assays to profile putative plasma biomarkers relevant to pancreatic and ovarian cancer, Clin. Chem. (2008) 5(3):582-89.
Fredriksson et al., Protein detection using proximity-dependent DNA ligation assays, Nature Biotech. (2002) 20:473-77.
Frese and Dierks, Formylglycine Aldehyde Tag-Protein Engineering through a Novel Posttranslational Modification, Chembiochem (2009) 10:425-27.
Fu et al., Counting individual DNA molecules by the stochastic attachment of diverse labels, PNAS, (2011) 108:9026-9031.
Gu et al., Protein tag-mediated conjugation of oligonucleotides to recombinant affinity binders for proximity ligation, N Biotechnol (2013) 30(2): 144-152.
Hammond et al., Profiling cellular protein complexes by proximity ligation with dual tag microarray readout, (2012) 7(7):e40405.
He, Cell-free protein synthesis: applications in proteomics and biotechnology, New Biotechnology (2008) 25:126-132.
He et al., In situ synthesis of protein arrays, Current Opinion in Biotechnology (2008) 19:4-9.
He et al., In situ synthesis of protein arrays, Current Opinion in Biotechnology (2008) 19:4-9 Supplementary figures.
He et al., Printing protein arrays from DNA arrays, Nature Methods (2008) 5:175-77.
Hedskog, et al., Dynamics of HIV-1 Quasispecies during Antiviral Treatment Dissected using Ultra-Deep Pyrosequencing, PLoS One, 5(7)e11345 (2010).
Hendrikson, et al., High sensitivity multianalyte immunoassay using covalent DNA-labeled antibodies and polymerase chain reaction, Nucl. Acid Res., 23 9):522-29 (1995).
Hiatt ,et al., Parallel, tag-directed assembly of locally-derived short sequence reads, Nature Methods, 7(2)119-25 (2010).
Hug, H. et al. Measurement of the number of molecules of a single species in a complex mRNA preparation. J. Theor. Biol. 221(4);615-624 (Apr. 21, 2003).
International Preliminary Report on Patentability Chapter I for PCT/US2010/033064, dated Nov. 1, 2011.
International Preliminary Report on Patentability Chapter I for PCT/US2010/044134, dated Jan. 31, 2012.
International Preliminary Report on Patentability Chapter I for PCT/US2010/059327, dated Jun. 12, 2012.
International Preliminary Report on Patentability Chapter I for PCT/US2011/031163, dated Oct. 9, 2012.
International Preliminary Report on Patentability Chapter I for PCT/US2011/031308, dated Oct. 9, 2012.
International Preliminary Report on Patentability Chapter I for PCT/US2012/032759, dated Oct. 8, 2013.
International Search Report and Written Opinion for PCT/US14/29691, dated Aug. 19, 2014.
International Search Report and Written Opinion for PCT/US2010/044134, dated Mar. 18, 2011.
International Search Report and Written Opinion for PCT/US2010/059327, dated Mar. 29, 2011.
International Search Report and Written Opinion for PCT/US2011/031308, dated Jun. 7, 2011.
International Search Report and Written Opinion for PCT/US2012/32759, dated Sep. 28, 2012.
International Search Report and Written Opinion for PCT/US2014/044191, dated Nov. 7, 2014.
International Search Report and Written Opinion for PCT/US2014/044196, dated Nov. 7, 2014.
International Search Report and Written Opinion of PCT/US14/64588, dated Mar. 11, 2015.
Invitation to Pay Additional Fees and, Where Applicable, Protest Fee for PCT/US2012/32759, dated Jul. 16, 2012.
Jabara, C.B. et al., Accurate sampling and deep sequencing of the HIV-1 protease gene using a Primer ID. PNAS 108(50); 20167 (2011).
Jones et al., Comparative lesion sequencing provides insights into tumor evolution. Proc. Natl. Acad. Sci. USA 105(11):4283-4288 (2008).
Kozlov et al., A High-Complexity Multiplexed Solution-Phase Assay for Profiling Protease Activity on Microarrays, Comb. Chem. High Throughput (2008) 11:24-35.
Kozlov et al., A Highly Scalable Peptide-Based Assay System for Proteomics, PLoS ONE(2012) 7(6):e37441.
Kozlov et al., A Method for Rapid Protease Substrate Evaluation and Optimization, Comb. Chem. High Throughput (2006) 9:481-87.
Kraytsberg et al., Single molecule PCR in mtDNA mutational analysis: genuine mutations vs. damage bypass-derived artifacts. Methods 46(4 ):269-273 (2008).
Kurz et al., cDNA-Protein Fusions: Covalent Protein-Gene Conjugates for the In Vitro Selection of Peptides and Proteins, Chem Bio Chem (2001) 2:666-72.
Larman et al., Autoantigen discovery with a synthetic human peptidome, Nature Biotechnology (2011).
Lasken, RS et al. Whole genome amplification: abundant supplies of DNA from precious samples or clinical specimens. Trends Biotechnol. 21(12); 531-535 (2003).
Lundberg et al., Homogeneous antibody-based proximity extension assays provide sensitive and specific detection of low-abundant proteins in human blood, Nucleic Acids Res.(2011) 39(15):e102.
Lundberg, et al., Multiplexed homogeneous proximity ligation assays for high-throughput protein biomarker research in serological material, Mol Cell Proteomics (2011) 10(4):M110.004978.
McCloskey, M.L. et al., Encoding PCR Products with Batch-stamps and Barcodes. Biochem. Genet. 45:761-767 (2007).
Mir et al., Sequencing by cyclic ligation and cleavage (CycLiC) directly on a microarray captured template, Nucleic Acids Res (2009) 37(1):e5.
Mizusawa, S. et al. A bacteriophage lambda vector for cloning with BamHI and Sau3A. Gene, 20(3); 317-322 (Dec. 1982).
Ng, et al., Massively parallel sequencing and rare disease, Human Molec. Genetics, 19(2):R119-R124 (2010).
Niemeyer, The developments of semisynthetic DNA/protein conjugates, Trends Biotechnol. (2002) 20(9):395-401.
Notice of Acceptance issued in Australian Patent Application No. AU 2011237729,dated Mar. 20, 2014, 6 pages.
Office Action for CA 2794522, dated May 22, 2014, 10 pages.
Office Action for U.S. Appl. No. 13/079,878, dated Aug. 13, 2012.
Office Action for U.S. Appl. No. 13/388,229, dated Dec. 24, 2012.
Office Action for U.S. Appl. No. 13/442,637, dated Jan. 22, 2015.
Office Action for U.S. Appl. No. 13/442,637, dated Aug. 9, 2012.
Office Action for U.S. Appl. No. 13/514,045, dated Feb. 21, 2013.
Office Action for U.S. Appl. No. 13/080,616, dated Apr. 9, 2014.
Oleinikov et al., Self-assembling protein arrays using electronic semiconductor microchips and in vitro translation, Journal of Proteome Research (2003) 2:313-319.
Osada et al., Epitope Mapping Using Ribosome Display in a Reconstituted Cell-Free Protein Synthesis System, J. Biochem. (2009) 145(5):693-700.
Patent Examination Report No. 1 for AU 2010278710, dated Feb. 11, 2014, 4 pages.
Patent Examination Report No. 1 for AU 2010328226, dated May 9, 2013.
Patent Examination Report No. 1 for AU 2011237729, dated Jul. 9, 2013.
Preliminary Amendment and remarks with filing of RCE for U.S. Appl. No. 13/442,637, dated Apr. 17, 2013.

(56) References Cited

OTHER PUBLICATIONS

Preliminary Amendment for U.S. Appl. No. 14/068,921, dated Nov. 22, 2013, 10 pages.
Proseek® Multiplex 96×96 User Manual (2013) Olink Bioscience, Uppsala, Sweden.
Ramachandran et al., Next-generation high-density self-assembling functional protein arrays, Nature Methods (2008) 5(6):535-38.
Request for Continued Examination for U.S. Appl. No. 13/080,616, dated Apr. 20, 2015, 15 pages.
Response to European Examination Report for EP 11766613.1, filed Jan. 8, 2015.
Response to Examination Report for European Patent Application No. EP 10836568.5, dated Jul. 10, 2014, 1 page.
Response to Examiner's Report for CA 2794522, filed Sep. 17, 2014, 28 pages.
Response to final Office Action for U.S. Appl. No. 13/080,616, filed Feb. 23, 2015, 17 pages.
Response to Final Office Action for U.S. Appl. No. 13/442,637, filed Mar. 20, 2013.
Response to First Examination Report for CN 201180017696.3, filed Mar. 3, 2014, 19 pages.
Response to First Examination Report for EP 10836568.5, filed Feb. 17, 2014, 10 pages.
Response to Office Action for CN 201180017696.3, filed Sep. 17, 2014, 16 pages.
Response to Office Action for U.S. Appl. No. 13/080,616, filed Aug. 11, 2014, pp. 1-22.
Response to Office Action for U.S. Appl. No. 13/442,637, filed Oct. 9, 2012.
Response to Office Action for U.S. Appl. No. 13/514,045, filed Jun. 17, 2013.
Response to Office Action for U.S. Appl. No. 13/514,045, filed Jun. 27, 2013.
Response to Patent Examination Report No. 1 for AU 2011237729, filed Mar. 3, 2014, 25 pages.
Response to Restriction Requirement for U.S. Appl. No. 13/080,616, filed Jan. 16, 2014, 11 pages.
Response to Restriction Requirement for U.S. Appl. No. 13/442,637, filed Jun. 5, 2012.
Response to Restriction Requirement for U.S. Appl. No. 13/514,045, filed Dec. 19, 2012.
Response to Rule 161/162 Communication for EP 11766613.1, filed May 17, 2013.
Response to Search Report for European Patent Application No. EP 11766613.1, dated Jul. 11, 2014, 1 page.
Response to Supplemental European Search Report for EP 10836568.5-1403, filed Sep. 10, 2013.
Response to Third Examination Report for CN 201180017696.3, filed Apr. 13, 2015.
Restriction Requirement for U.S. Appl. No. 13/080,616, dated Dec. 17, 2013, 6 pages.
Restriction Requirement for U.S. Appl. No. 13/442,637, dated May 17, 2012.
Restriction Requirement for U.S. Appl. No. 13/514,045, dated Nov. 23, 2012.
Roberts and Szostak RNA-peptide fusions for the in vitro selection of peptides and proteins, PNAS USA (1997) 94:12297-302.
Rouillard et al., OligoArray 2.0: design of oligonucleotide probes for DNA microarrays using a thermodynamic approach, Nucleic Acids Res. (2003) 31(12):3057-62.
Routenberg et al., Microfluidic probe: a new tool for integrating microfluidic environments and electronic wafer-probing, Lab Chip (2010) 10:123-127.
Rule 161/162 Communication for EP 11766613.1, dated Nov. 14, 2012.
Rush and Bertozzi, New Aldehyde Tag Sequences Identified by Screening Formylglycine Generating Enzymes in Vitro and in Vivo, J. of American Chemical Society (2008) 130:12240-41 Supplement.
Rush and Bertozzi, New Aldehyde Tag Sequences Identified by Screening Formylglycine Generating Enzymes in Vitro and in Vivo, J. of American Chemical Society (2008) 130:2240-41.
Search Report for PCT/US2010/033064.
Search Report for PCT/US2011/031163.
Shoemaker, et al. Quantitative phenotypic analysis of yeast deletion mutants using a highly parallel molecular bar-coding strategy. Nature Genetics, 14: 450-456 (1996).
Supplemental European Search Report for EP 10836568.5-1403, dated Mar. 4, 2013.
Supplemental Response and Amendment for U.S. Appl. No. 13/442,637, filed Jun. 6, 2012.
Supplementary European Search Report for EP 12767937.1, dated Nov. 18, 2014, 6 pages.
Takahashi and Roberts, In Vitro Selection of Protein and Peptide Libraries Using mRNA Display, Nucleic Acid and Peptide Aptamers: Methods and Protocols (2009) 535:293-314 (Ch. 17).
Taylor el al., Mitochondrial DNA mutations in human disease. Nat. Rev. Genet. 6(5):389-402 (2005).
Third Examination Report for CN 201180017696.3, dated Jan. 27, 2015.
Tolbert and Wong, New Methods for Proteomic Research: Preparation of Proteins with N-Terminal Cysteines for Labeling and Conjugation, Angew. Chem. Int. Ed. (2002) 41(12):2171-74.
Valencia et al., mRNA-Display-Based Selections for Proteins with Desired Functions: A Protease-Substrate Case Study. Biotechnol. Prog. 24:561-569 (2008).
Vogelstein and Kinzler, Digital PCR, PNAS USA, 96:9236-41 (1999).
Voluntary Amendment and Observation for CN 201180017696.3, filed Jul. 25, 2013.
Waichman et al., Functional Immobilization and Patterning of Proteins by an Enzymatic Transfer Reaction, Anal. Chem. (2010) 82:1478-85.
Weichhart et al., Functional Selection of Vaccine Candidate Peptides from *Staphylococcus aureus* Whole-Genome Expression Libraries In Vitro. Infection and Immunity, 71 (8):4633-4641 (2003).
Wong et al., Direct Site-Selective Covalent Protein Immobilization Catalyzed by a Phosphopantetheinyl Transferase, J. Am. Chem Soc. (2008) 130:12456-64.
Worthington et al., Cloning of random oligonucleotides to create single-insert plasmid libraries. Anal Biochem.294(2):169-75 (Jul. 15, 2001).
Xiao, et al., Direct determination of haplotypes from single DNA molecules, Nature Methods, 6(3):199-01 (2009).
Yin et al., Genetically encoded short peptide tag for versatile protein labeling by Sfp phosphopantetheinyl transferase. PNAS (2005) 102(44):15815-20.
Zhang et al., Assembling DNA through Affinity Binding to Achieve Ultrasensitive Protein Detection, Angew Chem Int Ed 2013 52:2-10.
Zhang et al., Binding-induced DNA assembly and its application to yoctomole detection of proteins, Anal Chem (2012) 84(2):877-884.
Zheng et al., Origins of human mitochondrial point mutations as DNA polymerase γ-mediated errors. Mutat. Res. 599(1-2):11-20 (2006).
Zhou et al., Genetically Encoded Short Peptide Tags for Orthogonal Protein Labeling by Sfp and AcpS Phosphopantetheinyl Transferases, ACS Chemical Biology (2007) 2(5):337-46.
Zlobec et al., Next-generation tissue microarray (ngTMA) increases the quality of biomarker studies: an example using CD3, CD5, and CD45RO in the tumor microenvironment of six different solid tumor types, Journal of Translational Medicine (2013) 11 :104.
U.S. Appl. No. 15/224,253 Non-Final Office Action dated Dec. 9, 2016.
U.S. Appl. No. 15/224,253 Non-Final Office Action dated May 18, 2017.

\* cited by examiner

NUCLEIC ACID CONSTRUCTS AND METHODS OF USE

CROSS-REFERENCE TO RELATED APPLICATIONS

This application is a divisional of U.S. patent application Ser. No. 13/266,568, filed Oct. 27, 2011, now allowed, which is a U.S. national stage application of International Patent Application No. PCT/US10/33064, filed Apr. 29, 2010, which claims benefit of priority to U.S. Provisional Application Ser. No. 61/174,442, filed Apr. 30, 2009, the contents of which are herein incorporated by reference in their entireties for all purposes.

STATEMENT REGARDING FEDERALLY SPONSORED RESEARCH OR DEVELOPMENT

This invention was made with the support by Grant Number 5R44HG004284, awarded by the National Human Genome Research Institute, National Institutes of Health, Department of Health and Human Services. The U.S. government may have certain rights in this invention.

FIELD OF THE INVENTION

This invention relates to the field of oligonucleotide selection and synthetic biology and nucleotide determination.

BACKGROUND OF THE INVENTION

In the following discussion certain articles and methods will be described for background and introductory purposes. Nothing contained herein is to be construed as an "admission" of prior art. Applicant expressly reserves the right to demonstrate, where appropriate, that the articles and methods referenced herein do not constitute prior art under the applicable statutory provisions.

Synthetic biology is a promising new field at the interface of engineering and biology. For review, see e.g., Endy D, Science. 2008 Feb. 29; 319(5867):1196-7. Recently parallel methods have been used to synthesize many different DNA sequences simultaneously, and to provide them as a pool of oligonucleotides. These and other effective methods for synthesizing relatively small pieces of DNA, typically up to a few kilobases in size, allow cost-effective production of large amounts of these oligonucleotides. With the availability of these high-quality, low-cost nucleic acid building blocks, much larger segments of DNA have been constructed. To date, these oligonucleotides have been used in the construction of an entire genome, the *Mycoplasma genitalium* genome, which is 583 kb (Gibson D G et al., PNAS USA. 2008 Dec. 23; 105(51):20404-9. Epub 2008 Dec. 10.)

Despite these advances, construction of multi-kilobase scale DNA molecules remains difficult and costly, largely because that de novo chemical synthesis of the DNA building blocks is quite error-prone. The intrinsic error rate of solid-phase oligo synthesis is thus a major limitation in the cost-effective assembly of larger DNA molecules. In addition, amplification steps that are used to increase the amount of starting material may also introduce errors, and certain large-scale oligonucleotide production methods may have an additional source of errors. Techniques required to identify and select oligonucleotides that are error-free—such as gel purification, bacterial vector cloning, comprehensive DNA sequencing, and enzymatic methods—are typically quite involved and not cost effective for wide-scale use in synthetic biology.

There remains a need to select error-free synthesized oligonucleotides for use in synthetic biology and other analytical methods. The present invention addresses this need by providing constructs, sets of constructs, and methods for ensuring accuracy of oligonucleotides having a desired sequence.

SUMMARY OF THE INVENTION

This Summary is provided to introduce a selection of concepts in a simplified form that are further described below in the Detailed Description. This Summary is not intended to identify key or essential features of the claimed subject matter, nor is it intended to be used to limit the scope of the claimed subject matter. Other features, details, utilities, and advantages of the claimed subject matter will be apparent from the following written Detailed Description including those aspects illustrated in the accompanying drawings and defined in the appended claims.

The present invention provides oligonucleotide constructs, sets of such oligonucleotide constructs, and methods of using such oligonucleotide constructs to provide validated sequences or sets of validated sequences corresponding to one or more desired sequences, i.e. "regions of interest". The use of the uniquely identifiable constructs of the invention to ensure the determination, selection and/or isolation of error-free regions of interest (ROIs) are correct is extremely effective, and allows specific sequences to be selected with high accuracy and high throughput. Such validated, error-free ROIs and constructs containing these error-free ROIs are useful in any technique that requires sequence fidelity, including the construction of larger molecules of known sequence, polymorphism and/or mutation screening, massively parallel sequencing, and quantification methods to preclude bias in the methodologies.

In one aspect, the invention provides a set of oligonucleotide constructs, where the constructs of the set comprise an ROI and an identifier unique to the individual construct. It is a fundamental element of the invention that the unique identifier is associated with a construct, not the ROI; thus, constructs with ROIs having the correct sequence can be differentiated from constructs having substantially the same ROI but containing errors. In general aspects, the constructs comprise one or more amplification sites to allow amplification of the construct and/or the ROI. For certain aspects, the constructs also comprise one or more excision sites to allow isolation the ROI from the remainder of the oligonucleotide construct.

Thus, in one aspect the invention provides a set of nucleic acid constructs, wherein the constructs of the set comprise an ROI, a unique identifier, and an amplification site, wherein the set of constructs comprises at least two constructs with substantially the same ROI and different unique identifiers. In some aspects, the set comprises at least five constructs with substantially the same ROI having different unique identifiers. In more specific aspects, the set comprises at least ten constructs with substantially the same ROI and different unique identifiers.

The number of nucleic acid constructs in a set should be large enough to ensure a high probability of obtaining at least one correct sequence or to confirm a correct sequence associated with a particular unique identifier. Therefore, the actual size of the set of constructs will depend on a number of factors, e.g., on the error rate of synthesis, the length of the nucleic acids constructs, and/or the ultimate purpose of the analysis. The distribution of frequencies of each of the ROIs in the pool may also impact on the size of the set of constructs.

In a specific aspect, the number of constructs in a set is based on the number of ROIs that can be confirmed in a given experimental operation using conventional techniques, e.g., sequencing capacity. For example, if one lane of a sequencing experiment obtains 10M reads, and the average redundancy of the constructs comprising an ROI is specified to be 100-fold to ensure a sufficiently high probability of obtaining at least one correct copy of an ROI, then a set of constructs of the invention would comprise approximately 100K separate constructs with unique identifiers. In practice, useful numbers of constructs in sets of the invention will depend on the current technology and the ultimate purpose of the set analysis.

In more specific aspects, the sets of the invention are populated by constructs comprising two or more amplification sites flanking the ROI and the unique identifier. These constructs allow the unique identifier and the ROI to be selectively amplified using conventional, two-primer amplification techniques such as the polymerase chain reaction (PCR). In certain aspects, the ROI and unique identifier are flanked by binding sites for a universal primer pair. In other aspects, the ROI and unique identifier are flanked by binding sites for a subset-specific primer pair. In other specific aspects, the ROI and unique identifier are flanked by binding sites for both universal primer pair and a subset-specific primer pair.

In other more specific aspects, the sets of the invention are populated by constructs comprising a single amplification site positioned to allow amplification of the ROI and the unique identifier. These constructs allow the unique identifier and the ROI to be selectively amplified using single primer-dependent amplification techniques such as asymmetric PCR.

In another general aspect the invention provides a set of nucleic acid constructs, wherein the constructs of the set comprise an ROI, a unique identifier, an amplification site, and an excision site, wherein the set of constructs comprises at least two constructs with substantially the same ROI and different unique identifiers. The excision site allows the ROI to be isolated from the constructs and used for various purposes, e.g., the construction of a larger nucleic acid comprising two or more ROIs. This allows the construction of a molecule with a validated, accurate sequence. In some aspects, the set comprises at least five constructs with substantially the same ROI having different unique identifiers and an excision site. In more specific aspects, the set comprises at least ten constructs with substantially the same ROI, different unique identifiers, and an excision site.

In specific aspects, the sets of the invention are populated by constructs comprising at least two excision sites flanking the ROI. This allows the ROI to be excised from any of the construct populations, including the initial selected subset of constructs, the amplified subset of constructs, or the master set of constructs.

In other specific aspects, the sets of the invention are populated by constructs comprising a single excision site adjacent the ROI. This allows the ROI to be excised from any of the construct populations, including the initial selected subset of constructs, the amplified subset of constructs, or the master set of constructs.

In a more specific aspect, the excision site may be created using a primer comprising a cleavable bond, e.g., a phosphorothioate, as set forth in Mag M. et al., Nucleic Acids Res. 1991 Apr. 11; 19(7):1437-41. Such cleavable sites allow excision at the 3' end of the primer on the strand incorporating the primer binding site.

The ROI for the present invention can be isolated from a natural or non-natural source, synthesized, or otherwise created. In some aspects, the ROIs of a set are fragments of a larger nucleic acid, and the constructs and methods used for sequence determination. In other aspects, the ROIs can be synthetic nucleic acids that are created for the production of larger molecules.

The different elements of the oligonucleotide constructs can be created by direct chemical synthesis with the ROI, or alternatively various elements of the construct can be added subsequently to synthesis or isolation of the ROI. The additional components can be added, for example, by ligation or via a primer in an amplification reaction. Such oligonucleotide constructs can be created in solution, on a solid support, or they may be added to a solid support following synthesis.

In one aspect of the invention, the constructs are synthesized and provided as free nucleic acids in solution.

In another aspect the constructs are created using fragmented nucleic acids, and the unique identifier and amplification regions are added to the individual fragments.

In yet another aspect, the oligonucleotides are provided immobilized on a support. In general, the constructs can be attached to the support in numerous ways, either directly or via a linker. In a specific aspect, the constructs can be synthesized first, with subsequent attachment to the support. In another specific aspect, the constructs are synthesized directly on the support. Such oligonucleotide constructs or their amplification products can be released from the support at various stages of the methods.

In a specific aspect of the invention, the unique identifier of the constructs is a degenerate nucleic acid sequence. The number of nucleotides in the identifier is preferably designed such that the number of potential and actual sequences represented by the identifiers is greater than the total number of oligonucleotide constructs in the set.

The invention also provides methods for isolating nucleic acids comprising ROIs from a set of oligonucleotides. The method involves isolating or identifying constructs from the set containing the desired ROIs, amplifying the isolated constructs, and isolating ROIs of the amplified constructs. Optionally, in one preferred aspect, the sequence fidelity of the amplified constructs is confirmed prior to the isolation of the ROIs from the constructs to ensure no errors have been introduced during the initial synthesis and/or amplification of the oligonucleotide constructs.

Thus, in a specific aspect, the invention provides a method for selecting nucleic acids having a desired sequence, comprising providing a set of oligonucleotide constructs comprising an ROI, a unique identifier, an amplification site, and an excision site; selecting constructs in the set containing the desired ROIs; amplifying all or a portion of the selected constructs; optionally validating the sequence fidelity of the amplified constructs; and identifying constructs having ROIs with the desired sequence. The specific constructs having validated ROIs (i.e., the ROIs confirmed as having the desired sequence) can be identified with specific unique identifiers—so the identifier is associated with the construct, not with the ROI itself.

The desired ROI can be excised directly from the master set, or from the selected constructs of the set that have undergone amplification. The methods of the invention thus further comprise isolating identified constructs from the master set of constructs of the invention, and excising the identified ROI from constructs in the master set. Alternatively or in conjunction, the identified ROI can be excised from a subset of constructs obtained from the master set, with such subset either being amplification products or an unamplified subset isolated from the master set.

The term "master set" as used herein not only encompasses the initial starting pool of constructs, but also in many practical applications a master set comprises a set of constructs resulting from a limited amplification or replication operation applied to the individual molecules of the initial set. A key element of a master set is the presence of a limited number of constructs comprising an ROI and a unique identifier. Where the master set includes amplification products of the initial constructs of a set, the number of copies in the set of amplified constructs substantially reflects the construct composition of the initial set.

The identified ROI with the desired sequence can optionally be excised from the constructs using various methods. For example, in certain specific aspects, the ROI is flanked by restriction endonuclease sites, and the ROI is excised using digestion with these specific endonucleases. In another example, the excision site contains a recognition site for a nickase, and the nickase is used to sever the ROI from the amplification site of the amplified construct. These isolated ROIs are useful in a variety of synthetic biology, discovery methods, and/or diagnostic methods. For example, the ROIs can be used as building blocks for the construction of larger nucleic acids. In another example, the ROIs can be used as a validated pool for the discovery or analysis of polymorphisms or mutations in a sample. In another example, the constructs of the invention comprising ROIs and unique identifiers can be used to identify potential bias in quantitative analysis introduced by utilized methodologies, or to assess fidelity of enzymes or methods used for amplification of certain sequences.

Thus, in one aspect, the methods of the invention are used in the construction of a larger nucleic acid molecule from shorter, validated nucleic acid molecules.

In another aspect, the methods of the invention are used for identifying potential sample bias introduced by quantitative analysis techniques.

In yet another aspect, the methods of the invention are used for determining the sequence of a larger nucleic acid by sequencing at least two constructs that are identical by descent for the ROIs of the set. This is especially useful for very complex sequencing sets or sequencing of nucleic acids having highly related sequences in different regions.

It is a feature of the invention that the different constructs have unique identifiers, including constructs that may have the same ROI, so the specific, correct ROIs can be distinctly identified and distinguished from the other constructs in the set. In essence, the 'unique' (i.e. unique for a construct comprising a particular ROI) identifiers are associated with individual molecules in the starting sample. Therefore, any amplification products of these initial individual molecules bearing the unique identifier are assumed to be 'identical by descent'.

Another feature of the invention is that it is more scalable and more accurate than traditional methods to enrich for sequences devoid of errors, such as of gel purification. Gel purification typically only reduces the number of insertion and deletion errors, but doesn't necessarily eliminate them; it is not particularly useful for removing substitution errors. The methods of the invention are also more effective that enzymatic discrimination or affinity selection, because the applications of the invention are both highly specific and highly parallel.

Yet another feature of the invention is that multiple oligos with different ROIs can be processed in a single reaction.

An advantage of the present invention is that it is designed specifically to minimize the need for amplification of desired sequences.

DEFINITIONS

Figure 1:
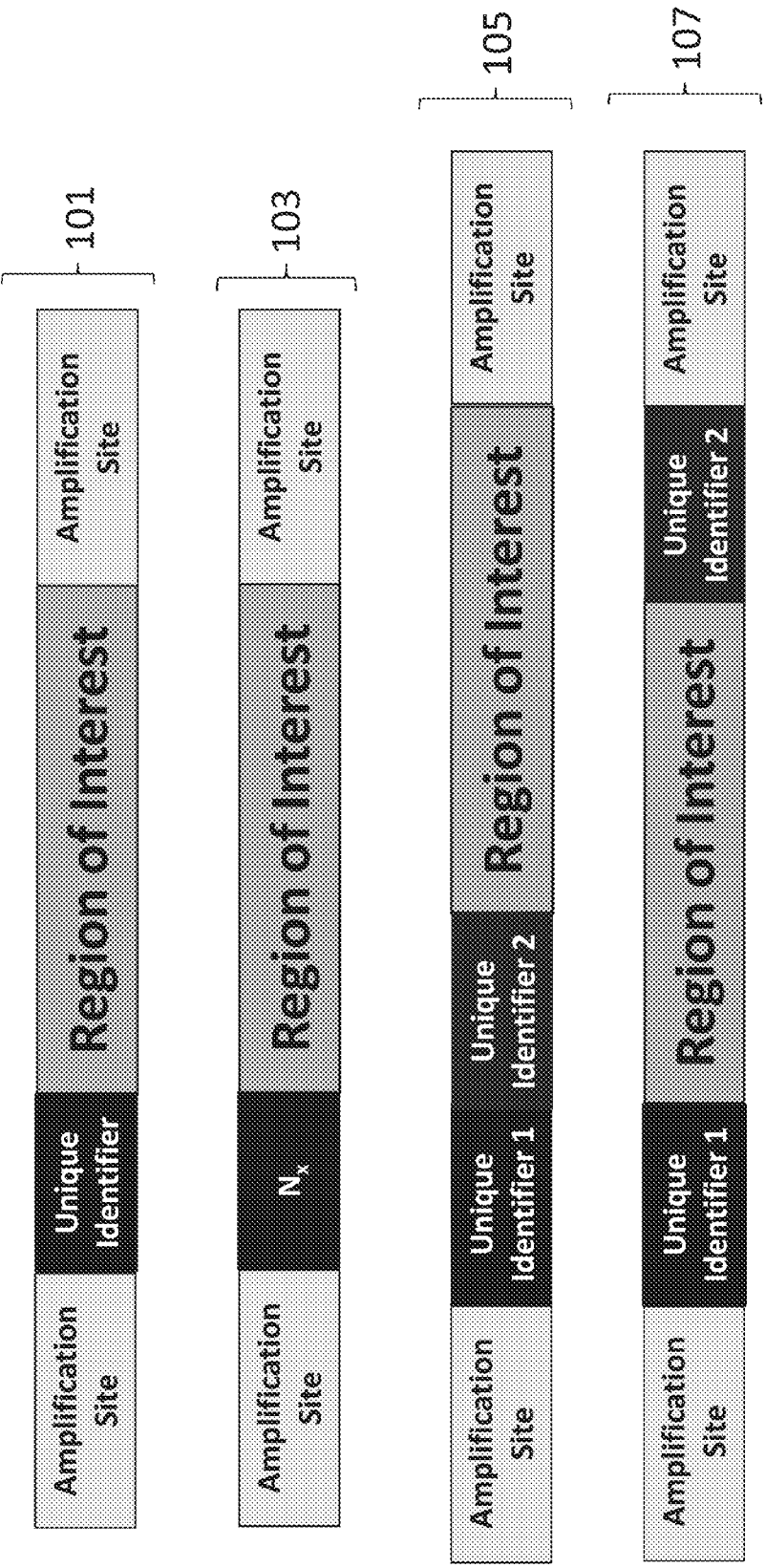
FIG. 1 is a schematic diagram showing exemplary constructs comprising an ROI, unique identifier(s) and two potential amplification sites for use in the various aspects of the invention.

The terms used herein are intended to have the plain and ordinary meaning as understood by those of ordinary skill in the art. The following definitions are intended to aid the reader in understanding the present invention, but are not intended to vary or otherwise limit the meaning of such terms unless specifically indicated.

"Complementary" or "substantially complementary" refers to the hybridization or base pairing or the formation of a duplex between nucleotides or nucleic acids, such as, for instance, between the two strands of a double-stranded DNA molecule or between an oligonucleotide primer and a primer binding site on a single-stranded nucleic acid. Complementary nucleotides are, generally, A and T (or A and U), or C and G. Two single-stranded RNA or DNA molecules are said to be substantially complementary when the nucleotides of one strand, optimally aligned and compared and with appropriate nucleotide insertions or deletions, pair with at least about 80% of the other strand, usually at least about 90% to about 95%, and even about 98% to about 100%.

"Hybridization" refers to the process in which two single-stranded polynucleotides bind non-covalently to form a stable double-stranded polynucleotide. The resulting (usually) double-stranded polynucleotide is a "hybrid" or "duplex." "Hybridization conditions" will typically include salt concentrations of approximately 1M or less, more usually less than about 500 mM and may be less than about 200 mM. A "hybridization buffer" is a buffered salt solution such as 5% SSPE, or other such buffers known in the art. Hybridization temperatures can be as low as 5° C., but are typically greater than 22° C., and more typically greater than about 30° C., and typically in excess of 37° C. Hybridizations are often performed under stringent conditions, i.e., conditions under which a primer will hybridize to its target subsequence but will not hybridize to the other, non-complementary sequences. Stringent conditions are sequence-dependent and are different in different circumstances. For example, longer fragments may require higher hybridization temperatures for specific hybridization than short fragments. As other factors may affect the stringency of hybridization, including base composition and length of the complementary strands, presence of organic solvents, and the extent of base mismatching, the combination of parameters is more important than the absolute measure of any one parameter alone. Generally stringent conditions are selected to be about 5° C. lower than the $T_m$ for the specific sequence at a defined ionic strength and pH. Exemplary stringent conditions include a salt concentration of at least 0.01M to no more than 1M sodium ion concentration (or other salt) at a pH of about 7.0 to about 8.3 and a temperature of at least 25° C. For example, conditions of 5.times.SSPE (750 mM NaCl, 50 mM sodium phosphate, 5 mM EDTA at pH 7.4) and a temperature of 30° C. are suitable for allele-specific hybridizations.

"Ligation" means to form a covalent bond or linkage between the termini of two or more nucleic acids, e.g., oligonucleotides and/or polynucleotides, in a template-driven reaction. The nature of the bond or linkage may vary widely and the ligation may be carried out enzymatically or chemically. As used herein, ligations are usually carried out enzymatically to form a phosphodiester linkage between a 5' carbon terminal nucleotide of one oligonucleotide with a 3' carbon of another nucleotide.

"Nucleic acid", "oligonucleotide", "oligo" or grammatical equivalents used herein refers generally to at least two nucleotides covalently linked together. A nucleic acid generally will contain phosphodiester bonds, although in some cases nucleic acid analogs may be included that have alternative backbones such as phosphoramidite, phosphorodithioate, or methylphophoroamidite linkages; or peptide nucleic acid backbones and linkages. Other analog nucleic acids include those with bicyclic structures including locked nucleic acids, positive backbones, non-ionic backbones and non-ribose backbones. Modifications of the ribose-phosphate backbone may be done to increase the stability of the molecules; for example, PNA:DNA hybrids can exhibit higher stability in some environments.

"Primer" means an oligonucleotide, either natural or synthetic, that is capable, upon forming a duplex with a polynucleotide template, of acting as a point of initiation of nucleic acid synthesis and being extended from its 3' end along the template so that an extended duplex is formed. The sequence of nucleotides added during the extension process is determined by the sequence of the template polynucleotide. Primers usually are extended by a DNA polymerase.

"Sequencing", "Sequence determination" and the like means determination of information relating to the nucleotide base sequence of a nucleic acid. Such information may include the identification or determination of partial as well as full sequence information of the nucleic acid. The sequence information may be determined with varying degrees of statistical reliability or confidence. In one aspect, the term includes the determination and ordering of a plurality of contiguous nucleotides in a nucleic acid.

The term "immobilized" as used herein refers to the association or binding between the nucleic acid construct and the support in a manner that provides a stable association under the conditions of amplification, excision, and other processes as described herein. Such binding can be covalent or non-covalent. Non-covalent binding includes electrostatic, hydrophilic, and hydrophobic interactions. Covalent bonds can be formed directly between the construct and the support or can be formed by a cross linker or by inclusion of a specific reactive group on either the solid support or the construct or both. Covalent attachment of a construct can be achieved using a binding partner, such as avidin or streptavidin, immobilized to the support and the non-covalent binding of the biotinylated construct to the avidin or streptavidin. Immobilization may also involve a combination of covalent and non-covalent interactions, as described further herein.

DETAILED DESCRIPTION OF THE INVENTION

The practice of the techniques described herein may employ, unless otherwise indicated, conventional techniques and descriptions of organic chemistry, polymer technology, molecular biology (including recombinant techniques), cell biology, biochemistry, and sequencing technology, which are within the skill of those who practice in the art. Such conventional techniques include polymer array synthesis, hybridization and ligation of polynucleotides, and detection of hybridization using a label. Specific illustrations of suitable techniques can be had by reference to the examples herein. However, other equivalent conventional procedures can, of course, also be used. Such conventional techniques and descriptions can be found in standard laboratory manuals such as Green, et al., Eds. (1999), *Genome Analysis: A Laboratory Manual Series* (Vols. I-IV); Weiner, Gabriel, Stephens, Eds. (2007), *Genetic Variation: A Laboratory Manual*; Dieffenbach, Dveksler, Eds. (2003), *PCR Primer: A Laboratory Manual*; Bowtell and Sambrook (2003), *DNA Microarrays: A Molecular Cloning Manual*; Mount (2004), *Bioinformatics: Sequence and Genome Analysis*; Sambrook and Russell (2006), *Condensed Protocols from Molecular Cloning: A Laboratory Manual*; and Sambrook and Russell (2002), *Molecular Cloning: A Laboratory Manual* (all from Cold Spring Harbor Laboratory Press); Stryer, L. (1995) *Biochemistry* (4th Ed.) W.H. Freeman, New York N.Y.; Gait, *"Oligonucleotide Synthesis: A Practical Approach"* 1984, IRL Press, London; Nelson and Cox (2000), Lehninger, *Principles of Biochemistry* $3^{rd}$ Ed., W. H. Freeman Pub., New York, N.Y.; and Berg et al. (2002) *Biochemistry*, $5^{th}$ Ed., W.H. Freeman Pub., New York, N.Y., all of which are herein incorporated in their entirety by reference for all purposes.

Note that as used herein and in the appended claims, the singular forms "a," "an," and "the" include plural referents unless the context clearly dictates otherwise. Thus, for example, reference to "an ROI" refers to one or more ROIs that may be present in a construct, and reference to "the selection method" includes reference to equivalent steps and alternative methods known to those skilled in the art, and so forth.

Unless defined otherwise, all technical and scientific terms used herein have the same meaning as commonly understood by one of ordinary skill in the art to which this invention belongs. All publications mentioned herein are incorporated by reference for the purpose of describing and disclosing devices, formulations and methodologies that may be used in connection with the presently described invention.

Where a range of values is provided, it is understood that each intervening value, between the upper and lower limit of that range and any other stated or intervening value in that stated range is encompassed within the invention. The upper and lower limits of these smaller ranges may independently be included in the smaller ranges, and are also encompassed within the invention, subject to any specifically excluded limit in the stated range. Where the stated range includes one or both of the limits, ranges excluding either both of those included limits are also included in the invention.

In the following description, numerous specific details are set forth to provide a more thorough understanding of the present invention. However, it will be apparent to one of skill in the art that the present invention may be practiced without one or more of these specific details. In other instances, well-known features and procedures well known to those skilled in the art have not been described in order to avoid obscuring the invention.

The Invention in General

The present invention provides a novel approach to ensuring sequence fidelity and/or quantifying the percentage of individual ROI sequences within a sample by creating nucleic acid constructs and selection methods for identifying particular ROIs in the constructs. The constructs of the invention have a unique identifier associated with the initial construct, thus giving the ability to differentiate between constructs having substantially the same ROI.

The ability to uniquely identify specific ROI-containing constructs (as opposed to identifying the same ROI present in multiple constructs) is critical in ensuring fidelity of the ROI in a particular construct, as it provides the ability to distinguish constructs comprising ROIs having errors from those with the correct sequence. It also allows the identification of technical bias in, say, amplification procedures used in quantitative analysis, as a skewed proportion of a specific construct in a sample can indicate a technical bias.

In addition, the unique identifiers allow confirmation of a specific construct comprising an ROI and its descendants, and allow identification of error that may be introduced due to the methods of determining a sequence of an ROI. Although massively parallel sequencing has advantages in cost and throughput, the accuracy of the reads can be comprised by the limitations of the amplification and/or detection technologies. The unique identifiers associated with a particular ROI confirm that the amplification molecules are related, and thus sequence differences between molecules with the same ROI can be identified as technical errors rather than real differences in the sequence (e.g., sequence differences from two copies of a similar sequence in a sample). Furthermore, because molecules that are identical by descent can be identified, a consensus sequence can be determined using data from multiple molecules, thereby achieving a much higher accuracy rate than most conventional high throughput methods.

These methods can be especially useful for applications involving large numbers of sequences that need to be determined, such as genomic sequencing. The improvement in accuracy resulting from the ability to determine whether ROIs are identical by descent provides a more sensitive method of detecting a rare sequence variant, such as a low-frequency mutation; or a minor allelic variant or haplotype in a sample containing DNA from multiple individuals. Thus a specific application of the methods of the invention is for confirmation of polymorphisms and mutations and/or for haplotype identification in genomic samples by providing distinguishing identifiers that are different for the different ROIs.

The unique identifiers of the present invention are in large part unique based on probabilities. The sets of constructs are designed so there is a large excess of possible identifiers relative to the ROIs in a given set. Thus, the chances of a having constructs with given identifiers associated with more than one ROI is very low, and the chances of the same identifier being associated with the same ROI in different constructs is extremely low. Thus, the term "unique" as used herein does not necessarily mean absolutely unique, but rather having an extremely high probability of being unique in its association with a particular ROI in a construct.

In a practical illustration of this concept, an aliquot can be taken from a master pool that has been amplified to have multiple copies of each ROI, with each ROI comprising a unique tag present in the initial constructs and their descendants. This aliquot can be sequenced directly, i.e. without competitive amplification. For example, certain non-competitive amplification steps may be allowed, including but not limited to solid-phase non-competitive amplification, such as cluster formation on the Illumina GA (San Diego, Calif.) platform, as they will minimize any skewing of results that are based on relative amounts or ratios of constructs in a set. A second aliquot from the amplified master set is then subject to further amplification and sequenced. Multiple first and second aliquots may be taken, to quantify sampling biases & effects of having different constructs for the same ROI. Random and systematic biases in amplification can then be detected by comparing the relative abundance of individual ROI-containing constructs pre- & post-amplification.

In another example, a master set is amplified prior to the sampling and sequencing, so that the first and second aliquots contain substantially the same constructs (i.e. constructs that are identical by descent). This may allow amplification bias to be detected for specific constructs (i.e., a specific ROI & identifier combination).

The invention has an advantage over conventional techniques for error detection, as it addresses three primary sources of error encountered in conventional synthetic biology and analysis of nucleic acids in biological samples—that is, errors in nucleic acid synthesis errors introduced in amplification of the original nucleic acid starting materials, and/or errors in sequence identification or determination caused by limitations of analytical methods. The methods and constructs of the invention recognize that such conventional techniques have limitations, and the methods of the invention work in conjunction with conventional molecular biology techniques to ensure accuracy of the desired sequences. The sets of molecules of the invention will contain some ROI sequences that are exactly those designed or isolated from a sample, and some that have errors introduced in the subsequent manipulation of such nucleic acids. The use of the sets of constructs and the methods disclosed herein allow one skilled in the art to identify the correct sequences within a master set or a selected subset of a master set, and can identify correct ROIs from ROIs that contain errors due to technical realities of chemical synthesis, amplification, and the like. In addition, the methods of the invention can identify technical bias in, e.g., amplification, as the unique identifier will be amplified with the ROI of each construct and thus the number of starting molecules can be inferred by association of each initial ROI present in a sample with its unique identifier.

One source of error the invention addresses is chemical synthesis or isolation and manipulation errors that are introduced during the initial synthesis and/or isolation of the nucleic acids comprising the ROIs. The second class of errors addressed by the constructs and methods of the invention includes errors that are introduced from the enzymatic amplification used to increase the amount of shorter nucleic acid fragments created through chemical synthesis. In addition, error can be introduced as a result of sequencing error; this can be overcome by sequencing multiple instances of the same ROI (i.e. identical by descent).

Even though very high fidelity polymerases are available, repeated copying increases the probability of errors. As a result, even a low error rate can have a significant impact, particularly in the construction of large molecules, such as entire genomes. The selection techniques of the invention minimize the need for amplification and decrease the likelihood that errors will be introduced following synthesis and/or isolation.

For example, the conventional approach for making larger nucleic acid molecules, including synthetic genomes, is first to carry out de novo chemical synthesis to generate oligonucleotides that are typically in the range of 20 to 200 nucleotides in length. A variety of methods are then be used to construct larger assemblies from these smaller oligos. For all presently known methods of producing double-stranded polynucleotides, however, the quality of the product is directly and exponentially dependent on the correctness of the employed oligonucleotides. In order to realize its full potential, new techniques such as the present invention are required to enable the construction of DNA molecules on a large scale and with high fidelity.

A feature of specific aspects of the invention is the use of nucleic acid sequences as the unique identifiers in the oligonucleotide constructs. These nucleic acid sequences provide diversity to the unique identifiers, e.g., by using a "degenerate" collection of sequences that can be randomly generated by synthesizing with a mixture of all four bases at each position. Alternatively, a diverse but pre-defined set of sequences can be synthesized and attached to the ROIs, e.g., via PCR primers or by ligation. The diversity of the identifiers needs to be sufficient so that molecules that are not related won't be mistaken as descendent ROIs. Thus, a "unique" identifier need not be absolutely unique, and may be used on different ROIs provided it is clear that they are different and not mistaken for a molecule that is identical by descent.

The large number of unique sequences that can be generated from the random assembly of nucleotides provides a high probability that each individual construct will be uniquely identified, even those constructs that contain substantially the same specific ROIs. The number of nucleotides in the identifier is preferably chosen so that the number of potential and actual sequences represented is much greater than the total number of oligonucleotide constructs in the set. For example, if the identifier comprises a 20-mer synthesized with a mixture of A, C, G and T at each position, there are $4^{20}$ possible sequences, i.e. approx. $10^{12}$. The use of such random identifiers allows even a large synthetic set to have constructs that can be individually distinguished.

In some aspects, the method of the invention allows the use of very small numbers of individual molecules to make desired larger synthetic constructs. In certain aspects, it is desirable to manipulate constructs and assembly intermediates in very small volumes to maintain relatively high concentrations. Thus, in certain aspects, the methods of the invention may utilize storage and sample processing in microfluidic environments and/or making using microfluidic systems to automate key processing steps, including those involved in construction of larger DNA assemblies.

In a specific aspect, the constructs and methods can be used more generally to identify and obtain any desired sequence from a collection of nucleic acid molecules. For example, the methods of the invention can be used to determine the sequence of naturally-occurring nucleic acids (e.g., DNA or RNA or fragments thereof that are isolated from a sample). These molecules can be used to create a master set of ROIs for sequence determination. When the starting nucleic acid is quite large, e.g., a genome or a complex mixture of nucleic acids, the sequences can optionally be assembled to result in one or more contiguous sequences containing two or more ROIs from the set. In other aspects, the ROIs can be used to create a large collection of smaller nucleic acids with extremely high sequence fidelity for any discovery research, diagnostic use, clinical use or other development techniques.

Creation of Master Set Constructs

The constructs of the invention can be created using a variety of techniques, and generally such techniques will be dependent upon the nature of the use of the construct.

For example, when the ROIs of the constructs are envisioned to be used in synthetic biology for construction of larger molecules, the construct can be synthesized as a single unit comprising the ROI, the unique identifier, and any other desired elements that may be necessary for further analysis, amplification, excision, and/or use of the constructs. The constructs can be synthesized as a single unit with all elements provided in a single synthesis step. This includes synthesis of the constructs in a liquid phase, such as parallel methods for simultaneous synthesis of many different DNA sequences. Single-step synthesis also includes synthesis directly on a substrate using, e.g., solid-phase synthesis. Alternatively, the various elements of the constructs, such as the amplification sites, the excision sites, the ROI, or any combination of these, can be individually synthesized and the construct assembled from these components using molecular biology techniques. In another example, when the constructs are to be used in quantitative analysis of nucleic acids derived from a biological sample, the nucleic acids containing the ROI are isolated, and the additional elements of the constructs are separately created and added to the sample nucleic acids using molecular biology techniques. This can be done in using a single group of sequences to provide the constructs for the master set. The construct assembly can also take place in smaller batches, e.g., to enhance the efficiency of the assembly processes, and the constructs pooled afterwards to populate the particular master set.

When a master set is created, in certain aspects it may contain more constructs that may be needed to achieve the desired representation of ROIs. In this aspect, an optional intermediate step may be used wherein a subset is sampled from the master set in to obtain a subset of a desired size, e.g., it would have roughly the same number of ROIs as the original master set, but the number of constructs would be restricted to a suitable number for the desired analysis and/or further manipulation. This 'restricted' subset could then be used as a master set for a given set of manipulations and analysis, and the remainder of the original master set stored for future use.

Selecting and Isolating Regions of Interest (ROIs)

Sets of oligonucleotide constructs comprising selected validated ROIs can be generated from a starting master set of constructs such as those oligonucleotides described in more detail herein. The steps involved in the selection and preparation of sets of ROI-containing constructs includes: identification and/or selection of a restricted number or "sample set" of constructs, amplification of such constructs, confirmation of accuracy of the ROIs of these constructs, and isolation of these ROIs.

Identification and/or Selection of Sample ROIs

In the methods of the invention, a subset of constructs can be obtained from the master set to obtain a restricted number of construct molecules. Constructs in the sample set can be selected based on random isolation of the constructs or via other mechanisms that can be based on the specific characteristics of the constructs. For example, a randomly selected subset of constructs from a master set can be isolated in solution and used for further testing to identify the constructs with the desired ROIs. In another example, a randomly selected subset of constructs from a set can be immobilized on a support for further amplification and determination of possible errors.

In yet another example, a specific subset of constructs can be selected using primers or a hybridization site on the construct that is specific to the subset. For example, labeled primers that bind to a common region of a subset of constructs can be hybridized to the master pool, and the subset isolated from this pool using, e.g., flow cytometry techniques. In another example, the subset may be immobilized to a support having oligonucleotides that are complementary to a substrate-specific binding region on the constructs.

The number of constructs in a subset necessary to ensure accuracy of the selected ROI or ROIs depends upon a number of factors, including but not limited to the length of the ROI, the error rate of the synthesis procedures, the error rate of other methods used to create the constructs, and the like. One skilled in the art, upon reading the present disclosure, will be able to identify these and other factors that together determine the number of constructs that need to be in the sample set in order to obtain the desired sequences.

For example, if it were determined that on average one would need 100 copies of each of 10,000 ROI sequences in order to have a probability near 1 of obtaining at least 1 perfect copy of each ROI sequence, then the number of constructs that would need to be selected from a master set of constructs would be targeted to be in the range of 1 million.

Amplification of ROIs

Following the selection of a set of constructs from a master set, the selected constructs undergo a limited amplification to provide additional material for determining accuracy of the ROI and the associated unique identifier that corresponds to an ROI. In certain aspects, the subset of constructs undergoes at least a 10-fold amplification, and more preferably a 100- to 1000-fold amplification. In some cases, even higher levels of amplification may be needed, e.g., a 10,000 to 100,000-fold amplification. In many circumstances, however, the extent of the amplification is minimized, and thus there is less opportunity for the introduction of errors from the amplification process.

In one example, universal primers that are complementary to the amplification sites in the constructs are used to perform a limited number of amplification cycles, so that each unique molecule now has a small number of identical copies each containing an ROI and the unique identifier. The number of copies obtained through this amplification procedure can be controlled at this step via the number of amplification cycles.

Amplification can be carried out in solution, using techniques such as PCR or emulsion PCR (with or without beads), and/or using solid-phase amplification, e.g., on a support surface. Conventional PCR amplification in solution may have the advantage that it is a simple and relatively inexpensive method for creating identical copies. Amplification by emulsion PCR or on solid-phase may have the advantage of better preserving the representation of different sequences in a complex mixture, which can be more important when larger numbers of amplification cycles are carried out.

In certain aspects, more than one amplification process can be used to expand the master set and/or the selected constructs for analysis. For example, an initial amplification of the master set in liquid phase can be carried out to expand the library. An aliquot of this material can then be further amplified to provide amplification of a subset, e.g., using universal primers in an aliquot of the master set or using subset-specific primers in the entire set or an aliquot of the master set. The second amplification may be useful to provide amplified material for sequencing, while the first ensures that sufficient material remains in the original library to enable subsequent use.

Confirmation of Accuracy

To ensure the ROIs in the selected constructs from the master set are error-free, various methods can optionally be used to ensure the fidelity of the sequence, including hybridization methods, enzymatic methods (e.g., Fuhrmann et al., *Nucleic Acids Res.* 2005 Mar. 30; 33(6):e58), and the like. In a specific aspect, selected constructs of the library, a specific subset of constructs from the library, or even the whole library can be sequenced. In certain circumstances, complete constructs are sequenced to confirm both the ROI and the unique identifier of a particular construct. In other aspects, only regions of particular concern (e.g., the ROI or even a portion of the ROI that is particularly susceptible to errors) can be sequenced, although it is preferably to sequence the entire molecule to ensure there are no introduced errors and to ensure identification of the construct based on the identifier.

In a preferred aspect, highly parallel next-generation sequencing methods are used to confirm the sequence of constructs. Such sequencing methods can be carried out, for example, using a one pass sequencing method or using paired-end sequencing. Next generation sequencing methods include, but are not limited to, hybridization-based methods, such as disclosed in Drmanac, U.S. Pat. Nos. 6,864,052; 6,309,824; and 6,401,267; and Drmanac et al, U.S. patent publication 2005/0191656, and sequencing by synthesis methods, e.g., Nyren et al, U.S. Pat. No. 6,210, 891; Ronaghi, U.S. Pat. No. 6,828,100; Ronaghi et al (1998), Science, 281: 363-365; Balasubramanian, U.S. Pat. No. 6,833,246; Quake, U.S. Pat. No. 6,911,345; Li et al, Proc. Natl. Acad. Sci., 100: 414-419 (2003); Smith et al, PCT publication WO 2006/074351; use of reversible extension terminators, e.g., Turner, U.S. Pat. No. 6,833,246 and Turner, U.S. Pat. No. 6,833,246 and ligation-based methods, e.g., Shendure et al (2005), Science, 309: 1728-1739, Macevicz, U.S. Pat. No. 6,306,597; which references are incorporated by reference. Soddart et al., *PNAS USA*. 2009 Apr. 20; Xiao et al., *Nat Methods*. 2009 March; 6(3):199-201. Epub 2009 Feb. 8.

In one particular aspect, the individual molecules are cloned onto beads and amplified using emulsion PCR to produce many copies of the original template on the surface of a bead. Thus, the sequencing method is essentially digital, as the sequence from one bead derives from an individual starting DNA molecule.

Although all existing sequencing mechanisms have an error rate, which varies by platform and according to other key variables, this can be overcome using the methods of the invention. Multiple instances of the same molecule can be sequenced, and the ROI of an individual parent construct can be identified by its unique identifier, as molecules with identical identifiers arise via amplification of the same original construct. Thus, a variation in the sequence of a single copy of a construct is most likely to be a synthesis or sequencing error if it differs from a consensus sequence derived from multiple clonal copies of the construct, which are identified as identical by descent via the shared unique identifier. Other methods of confirming fidelity generally rely on the accuracy of sequencing, and although the error rate can be decreased by repeating the sequencing process on the same templates or by sequencing both strands, these methods are not as accurate as the novel and efficient way of obtaining highly accurate ROI sequence validation provided by the present invention.

Following sequencing of the constructs, desired ROIs that are free of errors can be identified and the constructs and/or the ROIs of the constructs are optionally isolated. Importantly, such error-free ROIs can be subsequently identified by their unique identifier, which allows the constructs containing validated ROIs to be selected based on the identifier in either the subset or the master set of constructs.

Selection of Constructs with Desired Regions of Interest

Following identification of the validated constructs having the desired ROI and the unique identifier, such constructs are selected and/or isolated for further use.

For example, constructs that were subject to sequencing on support such as beads or a planar substrate can be recovered and the unique tags labeled using conventional techniques employing hybridization and labeling. For example, when constructs have been amplified and sequenced directly on beads, the selected constructs on the beads can be labeled by hybridization of such tags that bear a detectable label and are complementary to the unique identifier. The positive beads can then be collected by flow sorting, capture mechanisms, or other equivalent means known to those in the art.

In specific aspects of the invention, affinity capture can be used to isolate desired constructs containing validated ROIs. For example, a primer complementary to the unique identifier (or the unique identifier itself) can be immobilized and used to bind to the desired construct. In another example, oligos complementary to the unique identifier (or the unique identifier itself) can comprise one element of a binding pair, such as a biotin molecule. This binding molecule can be used to capture the oligos via its binding partner, e.g., avidin or streptavidin, which is preferably provided on beads or another solid support.

In a preferred embodiment, identification of the unique identifier is used to select the appropriate constructs form a minimally amplified master set. In such a case, rather than isolating the amplified material that was subject to analysis to confirm sequence of an ROI, the information obtained from the subset is used to associate a unique identifier with a correct ROI, and a unique tag for the particular identifier used to isolate the correct construct directly from the master set. This can be accomplished using numerous methodologies, including but not limited to the exemplary methods that follow.

In one example, the constructs of interest can be identified using hybridization methods, including hybridization of the constructs comprising the unique identifier to a microarray or other nucleic acid construct platform. An array can be designed that contains oligos that are complementary to the unique identifiers corresponding to the desired, validated ROIs. The set of oligonucleotide constructs in the master set is hybridized to the array to enrich for the desired sequences. This process can be repeated to ensure appropriate enrichment of the desired constructs. Enrichment can also be carried out sequentially using more than one complementary oligo to provide orthogonality and minimize errors in capture of the constructs.

In another example, a labeled tag is hybridized directly to the unique identifier to label the desired molecules. Once labeled, these constructs can be selected using a sorting technology. For example, beads comprising identical constructs containing the desired ROI (such as the identical construct copies resulting from emulsion PCR) can be labeled by hybridization of capture oligonucleotides that are complementary to the unique identifier, and the beads comprising the desired construct isolated using methods such as flow cytometry.

The purity of the sorted sequences will depend primarily on the accuracy of labeling by hybridization and the accuracy of sorting. The former can be increased by hybridizing to a second sequence (which may be overlapping with the first), to overcome systematic errors. The latter can be improved by repeating the sorting method to ensure accuracy and/or improve yield.

To truly minimize the amount of amplification needed, the labeling and sorting of individual molecules can be employed prior to the amplification step in the present methods. Such methods can include, for example, single molecule analysis such as that provided by U.S. Genomics (Woburn, Mass.); or other similar technologies for sorting and enriching the individual tagged molecules.

In certain circumstances, desired constructs may be sequentially isolated from the sets. For example, it may be desirable to assemble validated oligos in a modular fashion, and to group together subsets of sequences to accomplish this with minimal risk of non-specific interactions. This can be accomplished by using two or more sets of amplification primers. Thus, in some aspects of the invention, such as the exemplary constructs shown in FIGS. 5 and 6, different sets of primer binding sites can be used within a construct. Although these are illustrated in the figures as separate, distinct sites, the amplification site of one of the primers may overlap with the recognition site of a different primer. In some aspects, the primer binding sites bind a pair of universal primers, while the other binding sites bind a pair of subset-specific primers. In certain aspects, the subset-specific binding pair actually utilizes one of the universal primers, and thus only three binding sites would be necessary in the construct to provide both universal and subset-specific amplification. Use of different primer pairs can allow the selection of a subset of constructs using the more specific primers, while still allowing for the amplification of the entire set of constructs (including those in the subset) via the universal primers.

By way of illustration but not limitation, rather than isolating and using 10,000 sequences, it may be preferable to isolate 100 groups of 100 sequences each. This can be accomplished using the aid of 100 pairs of subset-specific primers instead of two universal primers in the amplification of the constructs. These primers can be used instead of or in addition to the universal primer set. If used instead, 100 separate amplifications would be carried out. All 100 samples could then be pooled for sequencing, and the correct sequences selected from the 100 master sets. Of course, other variations of this strategy could be used. For example, rather than amplifying the master set desired subsets can be amplified at a convenient point in the process by using the subset-specific primer pairs.

One reason for choosing to amplify subsets of sequences is to facilitate the construction of larger molecules. Although it may be possible to assemble 10,000 or more molecules simultaneously with sufficient specificity, this process can be simplified by assembly in stages, i.e. initial assembly of portions of the molecules, and subsequent assembly of these portions. This can simplify the construction process for these larger nucleic acids and improve yields.

Isolation of ROIs from the Constructs

Once constructs comprising the ROIs of desired sequence have been identified, the discrete ROI of these constructs can be isolated for further use, e.g., as building blocks for larger molecules or for quantitative analysis studies. The excision site(s) in the constructs will facilitate this isolation, and various methods are available in the art to selectively remove the ROIs from either the master set or the subsets. The excision sites available in particular constructs will tend to dictate the best methods to isolate specific ROIs from the construct.

In one aspect, the excision site(s) used in the construct are restriction endonuclease sites, and the ROI is removed from the constructs using conventional enzymatic cleavage techniques. A wide variety of restriction endonucleases are available for this use, and include any identified enzyme that cuts double-stranded or single stranded DNA at specific restriction sites within the constructs. Examples of such enzymes are found in the REBASE database (Roberts, R. J., et al., (2007) *Nucl. Acids Res.* 35: D269-D270).

In certain aspects, the excision sites comprise recognition sites for enzymes with rare cleavage sites to decrease the likelihood that the enzyme will cleave in a specific ROI. Such enzymes with long (and therefore rare) recognition sites can be used to reduce the risk that the cleavage will occur within the actual ROI, as these recognition sites occur rarely in a genome. Exemplary restriction enzymes with rare recognition sites include, NotI, AscI, FseI, PacI, PmeI, Sse8387I, SacI, SalI, SphI; SgfI; SrfI, SdaI; and SgrAI.

In some aspects, it may be useful to use methylation-sensitive restriction enzymes to excise the ROI, as methylation methods can be used to control the timing of cleavage or to limit the specific constructs that are cleaved. Such restriction enzymes include, but are not limited to, AatII, AjiI, BstUI, Bsh1236I, Bsh1285I, BshTI, Bsp68I, Bsp119I, Bsp143II, Bsu15I, CseI, Cfr10I, Cfr42I, CpoI, Eco47III, Eco52I, Eco72I, Eco105I, EheI, Esp3I, FspAI, HhaI; Hin6I, Hin1I, HpaII, Kpn2I, MluI, NotI, NsbI, PauI, PdiI, Pfl123II, Ppu21I, Psp1406I, PvuI, SalI, SgsI, SmuI, SsiI, TaiI, and TauI.

In particular aspect, Type IIS restriction enzymes are used, as these can be designed to cut in the ROI itself and leave no remnant of the other elements of the construct. Type IIS enzymes cleave a site adjacent to their asymmetric binding region, and thus allow cleavage in a site a small distance away from the recognition site. For synthetic biology uses, designing IIS sites into the construct can be used to generate sticky ends for further manipulation, yet also leave no contaminant sequences left from the construct in the final ROI. Exemplary Type IIs restriction endonucleases include, but are not limited to, Eco57M I, Mme I, Acu I, Bpm I, BceA I, Bbv I, BciV I, BpuE I, BseM II, BseR I, Bsg I, BsmF I, BtgZ I, Eci I, EcoP15 I, Eco57M I, Fok I, Hga I, Hph I, Mbo II, Mnl I, SfaN I, TspDT I, TspDW I, Taq II, and the like.

In one aspect, the excision site of the construct comprises a nickase enzyme digestion site or other nickable site. Nickases are endonucleases that recognize a specific recognition sequence in double stranded DNA, and cut one strand at a specific location relative to said recognition sequence, thereby giving rise to single-stranded breaks in duplex DNA. Nickases include but are not limited to Nb.BsrDI, Nb.BsmI, Nt.BbvCI, Nb.BbvCI, Nb.BtsI and Nt.BstNBI. Use of a nickase on the double-stranded amplification product results in a single-stranded nick, and in specific aspects of the invention can release a ss ROI region from an oligonucleotide that is fused to a support upon denaturation. This can be useful to generate single-stranded ROIs for detection, as in quantification and/or diagnostic methods. The ss ROI can also optionally be converted to a ds molecule using one or more ROI-specific primers.

In addition to the use of restriction endonucleases and nickases, the ROIs of the constructs of the invention may be excised using a variety of mechanisms. The following are exemplary methods for doing so. Other methods within the spirit of the invention will be apparent to those skilled in the art upon reading the present specification.

Thus, in one aspect, an ROI may be removed from a construct using an artificial site-specific DNA cutter. These agents usually contain a complex consisting of a chelator and an appropriate metal or a catalytic domain of a restriction enzyme that is capable of cleaving DNA. In order to insure site-specific DNA cleavage, this complex is usually attached to one of the following: a sequence-specific DNA binding drug; a terminus of a synthetic sequence-specific DNA binding peptide; multiple positions of a sequence-specific DNA binding protein; an oligonucleotide capable of forming triple helix; peptide nucleic acids (PNAs) (with poly[N-(aminoethyl)glycine] backbone) or their analogues; minor-groove binding sequence specific polyamides containing aromatic ring amino acids (for example: pyrrole-imidazole polyamides); a single, defined position within a DNA binding protein or motif. See, e.g., Ebright R H et al. (1990) PNAS USA 87: 2882-2886; Hélène C (1993) Curr Opin Biotechnol 4: 29-36; Chang A Y and Dervan P B (1994) Science 266: 646-650; Smith J, et al., (2000) Nucleic Acids Res 28: 3361-3369; Nakatsukasa T et al. (2005) Biochem Biophys Res Commun 330: 247-252; Eisenschmidt K et al. (2005) Nucleic Acids Res 33: 7039-7047. Mancin F, et al., (2005) Chem Commun (Camb): 2540-2548; Yamamoto Y et al., (2007) Nucleic Acids Res 35: e53; Yamamoto Y et al. (2006) Chembiochem 7: 673-677; and Katada H and Komiyama M (2009) Artificial Restriction DNA Cutters as New Tools for Gene Manipulation. *Chembiochem.*

In another example, catalytic nucleic acids can be used to provide an excision site. DNA sequences can be designed to be self-cleaving. Alternatively, DNA or RNA based catalysts cut DNA is a site-specific manner. See, e.g., Carmi N and Breaker RR (2001) Bioorg Med Chem 9: 2589-2600; Sen D and Geyer C R (1998) Curr Opin Chem Biol 2: 680-687; Emilsson G M and Breaker R R (2002) Cellular and Molecular Life Sciences (CMLS) 59: 596-607; and Cairns M J et al., (2002) Curr Drug Targets 3: 269-279.

In yet another example, site-specific DNA cleaving enzymes other than naturally occurring restriction endonucleases can be used to provide an excision site in the constructs of the invention. Examples include but not limited by topoisomerases; transposases, recombinases; and integrases. These enzymes and also naturally occurring restriction endonucleases can be altered (re-designed using standard molecular biology protocols) in order to fit specific applications and/or uses of the methods and constructs of the invention. See, e.g., Fortune J M et al., (2002) Biochemistry 41: 11761-11769; Kolb A F (2002) Cloning & Stem Cells 4: 65-80; Akopian A and Stark W M (2005) Advances in Genetics 55:1; and Coates C J et al., (2005) Trends Biotechnol 23: 407-419.

In yet another example, chemical methods for DNA cleaving can be used to excise ROIs from the constructs of the invention. For example, one ribonucleotide can be incorporated at the junction of the primer and the ROI. Alkaline or ribonuclease hydrolysis will cause oligonucleotides to hydrolyze at the position of the ribonucleotide, resulting in a 5' hydroxyl group at the end of the target sequence. Another example is to use a phosphorothioate substitution at the junction of the primer and the target oligonucleotide sequence. The site of phosphorothioate incorporation is readily cleaved iodine. See, e.g., Gish G and Eckstein F (1988) Science 240: 1520-1522; Strobel S A and Shetty K (1997) PNAS USA 94: 2903-2908.

Immobilized Constructs

In certain aspects of the invention, the sets of constructs of the invention can be attached to or immobilized on a support in a wide variety of ways. As described herein, the nucleic acids can either be synthesized first, with subsequent attachment to the biochip, or can be directly synthesized on the support. By "substrate" or "solid support" is meant any material with discrete individual sites appropriate for the attachment or association of the nucleic acid constructs and that is amenable to at least one detection method. As will be appreciated by practitioners in the art, the number of possible substrates are very large, and include, but are not limited to, glass and modified or functionalized glass, plastics (including acrylics, polystyrene and copolymers of styrene and other materials, polypropylene, polyethylene, polybutylene, polyurethanes, Teflon™, etc.), polysaccharides, nylon or nitrocellulose, resins, silica or silica-based materials including silicon and modified silicon, carbon, metals, inorganic glasses, plastics, etc. In general, preferred substrates do not appreciably fluoresce, thus allowing optical detection of labeled primers or tags.

In some aspects, the substrate is planar, although other configurations of substrates may be used as well. For example, the constructs may be placed on the inside surface of a tube, for flow-through sample analysis to minimize sample volume including cells made of particular materials. The substrate may also be flexible, such as a film, membrane or other flexible structure.

In a particular aspect, the substrates used are beads, e.g., pore-glass beads, silica gels, polystyrene beads optionally cross-linked with divinylbenzene, grafted co-poly beads, polyacrylamide beads, latex beads, dimethylacrylamide beads optionally crosslinked with N—N'-bis-acryloylethylenediamine, iron oxide magnetic beads, and glass particles coated with a hydrophobic polymer). The use of smaller, discrete substrates such as beads is preferred in certain circumstances, and beads may be particularly useful in certain amplification methods, such as emulsion PCR. In certain circumstances, it may be desirable to have beads with an attribute that facilitates their isolation, such as activated or magnetic beads. The use of beads may be particularly desirable for use with certain amplification methods, such as emulsion PCR.

In aspects, oligonucleotides constructs are synthesized on the substrate. For example, photoactivation techniques utilizing photopolymerisation compounds and techniques can be used. In an illustrative example, the nucleic acids are synthesized in situ, using well known photolithographic techniques, such as those described in WO 95/25116; WO 95/35505; U.S. Pat. Nos. 5,700,637 and 5,445,934; and references cited within; these methods of attachment form the basis of the Affymetrix GeneChip™ technology.

In other aspects, the oligonucleotides may be synthesized and subsequently immobilized on a substrate. In such aspects, the surface of the substrate is preferably modified to allow oligonucleotide attachment, e.g., by providing linker groups, binding pair members on discrete sites on the surface. In other aspects, the substrate surface is treated with a chemical that facilitates oligonucleotide attachment, and the oligonucleotides are distributed onto discrete sites, such as illustrated in U.S. Pat. No. 6,498,245 or distributed randomly on the surface.

Specific Examples of the Constructs and Methods of the Invention

Specific examples of oligonucleotide constructs and amplification mechanisms that may be used for various oligonucleotide constructs are illustrated in FIGS. 1-13. The examples are not meant to be limiting, as various other elements can be added to the constructs, and the orientation of the constructs can be altered from that illustrated in these examples, as will be apparent to one skilled in the art upon the reading of the present disclosure.

FIG. 1 sets forth more general constructs for use in the methods of the invention. These comprise an ROI, a unique identifier, and one or more amplification sites. The figures actually illustrate constructs comprising two amplification sites flanking the ROI and the unique identifier, such as the general constructs illustrated at 101. In 101, one amplification site is found substantially at the 5' end of the oligonucleotide and the other provided substantially at the 3' end of the oligonucleotide. The unique identifier that distinguishes each initial construct from the other initial constructs in the master set and the ROI are within the regions that are amplified using the two flanking sites. The construct of 103 has the same configuration as 101, but is more specific in that the unique identifier is a tag comprising nucleotides of varying sequence.

The number of nucleotides used in the identifier will be determined in part by the number of different constructs that are to be produced in a set, but may range from a few nucleotides to up to 10, 20 or even 30 or more nucleotides in different sequence arrangements. In some cases, it is useful to use an additional unique identifier, as illustrated in the constructs 105 and 107. The second unique identifier can either be found on the same side of the ROI, as in 105, or flanking the ROI, as in 107. The use of two or even more unique identifiers can allow the use of shorter individual identifiers and/or two or more smaller "subsets" of constructs due to the uniqueness conferred by the combination of the two tags.

Figure 2:
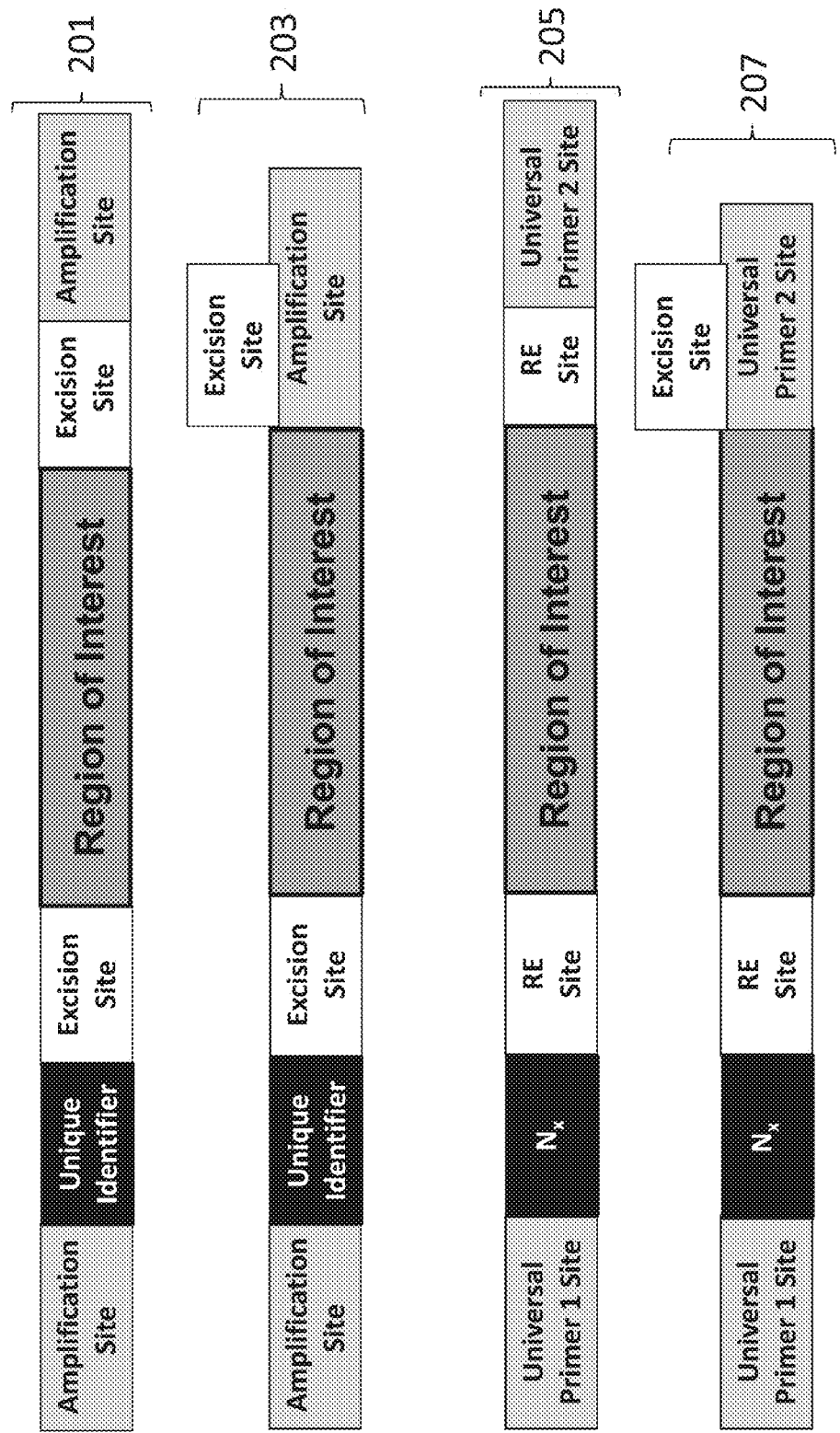
FIG. 2 is a schematic diagram showing exemplary constructs comprising two potential amplification sites and two excision sites for use in a first aspect of the invention.

FIG. 2 is a schematic diagram showing different examples of one class of oligonucleotide constructs that can be used in the sets and methods of the present method. These oligonucleotides contain elements designed for use with any conventional, bi-directional amplification method such as the polymerase chain reaction. In these constructs, the ROI and the unique identifier are flanked by two or more excision sites and two or more amplification sites. In each of these examples, the amplification sites may be identical at each end, thus enabling the use of one primer to amplify the unique identifier and the ROI, or more preferably the two amplification sites are different from one another but the same in each unamplified construct regardless of ROI or unique identifier. In addition, different amplification sites can be designed so that two or more primer pairs can be used for amplification of the construct or specific elements thereof.

In FIG. 2, constructs 201 and 203 are general schematics of single-stranded constructs comprising: two amplification sites, one found substantially at the 5' end of the oligonucleotide and the other provided substantially at the 3' end of the oligonucleotide; a unique identifier that distinguishes each initial construct from the other initial constructs in the master set; and excision sites that allow the separation of the ROI from the remaining element of the construct, thus enabling separation and isolation of the ROI for further use in various synthetic biology, quantitative measurement, or other methodologies. In Construct 1A, the amplification site that is opposite the unique identifier is separate from the adjacent excision site, whereas in Construct 203 the excision site is designed to be a part of the amplification site. Constructs 205 and 207 illustrate preferred aspects of such constructs of the invention, in which the unique identifier is a degenerate nucleic acid sequence, and the excision sites comprise restriction endonuclease cleavage sites.

Figure 3:
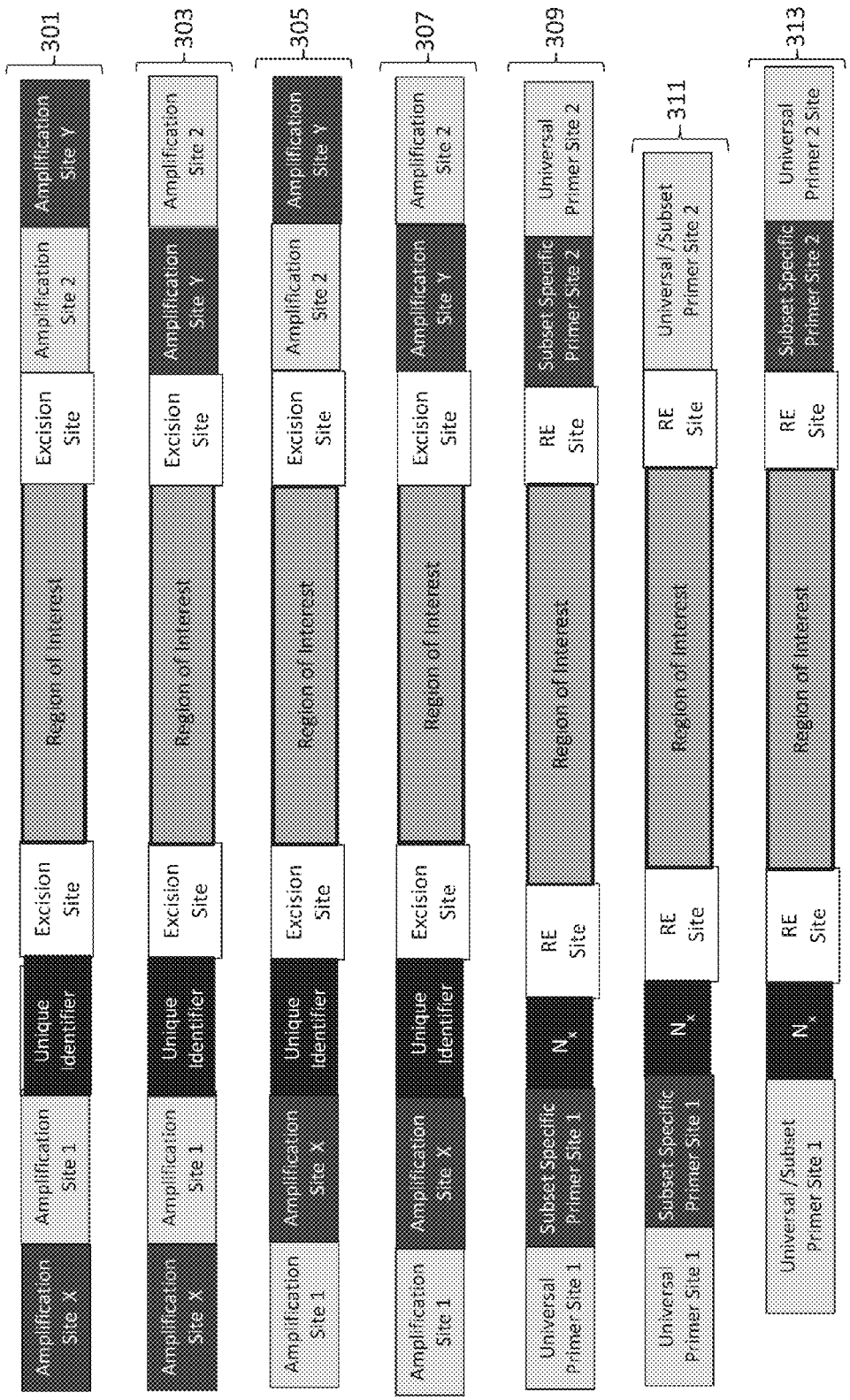
FIG. 3 is a schematic diagram showing exemplary constructs comprising two potential amplification sites and two excision sites for use in a second aspect of the invention, where the constructs are immobilized on a substrate.
Figure 4:
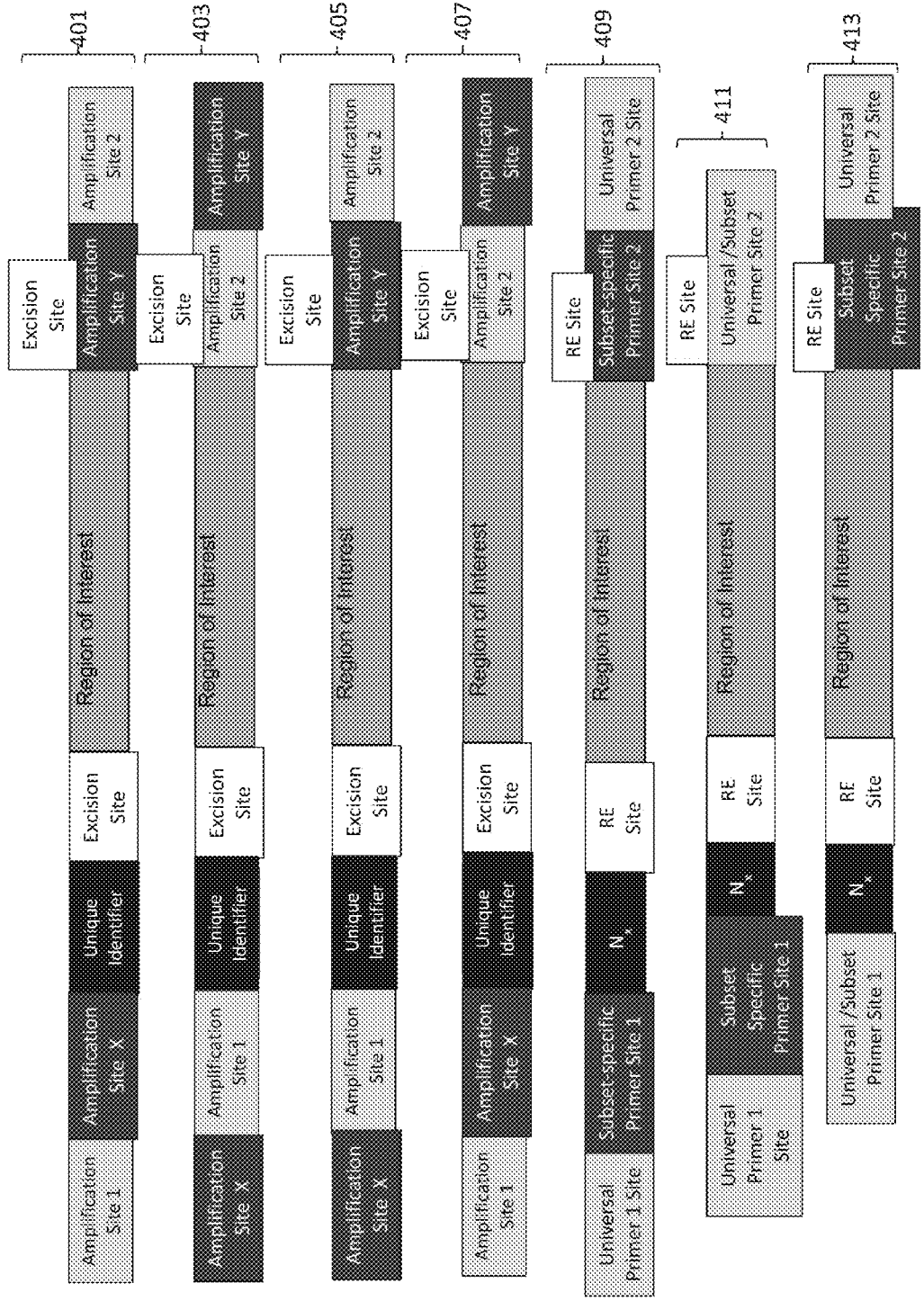
FIG. 4 is a schematic diagram showing exemplary constructs comprising two potential amplification sites and two excision sites for use in a third aspect of the invention, where the constructs are immobilized on a substrate.

FIGS. 3 and 4 illustrate constructs having two pairs of amplification sites, with exemplary constructs of FIG. 3 having separate excision regions, and the exemplary constructs of FIG. 4 having at least one of the excision sites overlapping with an amplification site. In certain specific aspect, both pairs of amplification sites bind universal primers, and thus two sets of universal primers may be used in the amplification scheme. Examples of different potential orientations of these are provided in constructs 301-307 and 401-407. In these constructs, amplification sites can be designed so that: two sets of universal primers can be used for amplification; one set of universal primers or and one subset-specific primer pair can be used for amplification; or two sets of subset-specific primers can be used, in the case where a single ROI may belong to two or more specific subsets. Preferably, however, one pair of amplification sites comprises universal primer binding sites, while the other pair of amplification sites are binding sites for subset-specific primers, as shown in 309 and 409 in FIGS. 3 and 4. This will provide both general amplification methods for all of the constructs in the set as well as a more specific mechanism for amplifying the constructs of a desired subset. Also, in these preferred aspects, the unique identifiers are preferably comprised of degenerate oligonucleotides.

As will be apparent to those skilled in the art upon reading the present disclosure, many other combinations of two or more amplification sites may be used. The constructs may also include other amplification sites, for example another set of subset-specific primer sites for the same or a different subset, or an additional universal primer amplification set. In addition, one universal primer could be used with a subset-specific amplification site, so that only three primers total would be necessary for both the universal amplification and the subset-specific amplification, as illustrated in 311, 313, 411, and 413 in FIGS. 3 and 4. Although these constructs illustrate one orientation of the two amplification sites, they may also be present at different positions on the molecule. Alternatively or in addition, an amplification site can be placed between the left excision site and the ROI. This could be used, e.g., for excision via a 3' cleavable primer.

Figure 5:
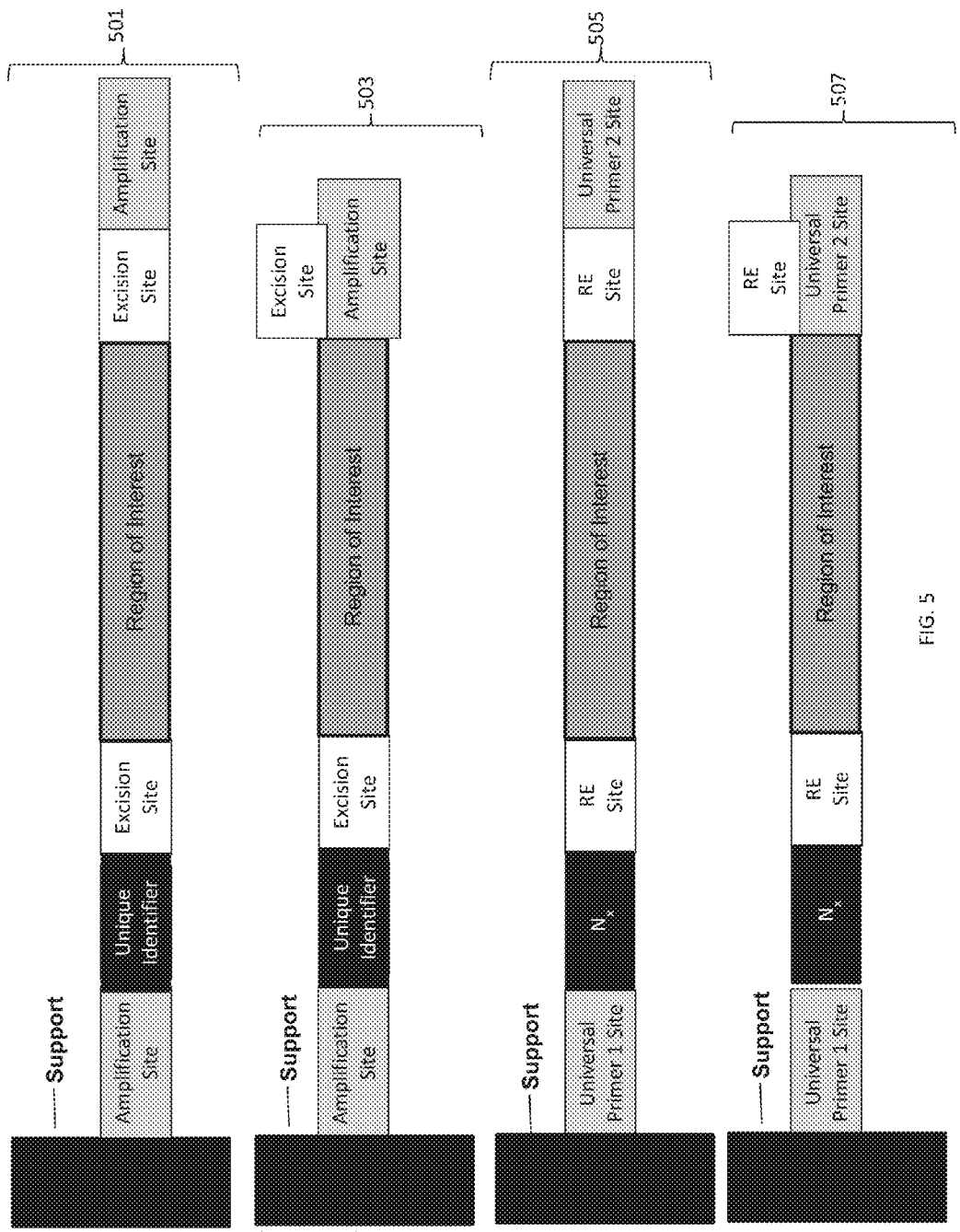
FIG. 5 is a schematic diagram showing exemplary constructs comprising four potential amplification sites and two excision sites for use in a fourth aspect of the invention.

In FIG. 5, the constructs themselves are similar to those illustrated in FIG. 2, except the constructs are immobilized directly on a support. In 501 in FIG. 5, the amplification site that is opposite the unique identifier is separate from the adjacent excision site, whereas in 502 the excision site is designed to be a part of an amplification site. Constructs 505 and 507 in FIG. 5 illustrate preferred aspects of such constructs of the invention attached to substrates, in which the unique identifier is a degenerate nucleic acid sequence, and the excision sites comprise restriction endonuclease cleavage sites. Although the constructs are shown in FIG. 4 attached with the unique identifier 5' to the ROI with respect to support attachment, the molecules may be immobilized to the support in either orientation, and thus the construct components may be in the opposite order to that illustrated. The constructs illustrated in FIGS. 3 and 4 can also be used attached to supports in this fashion (not shown).

Figure 6:
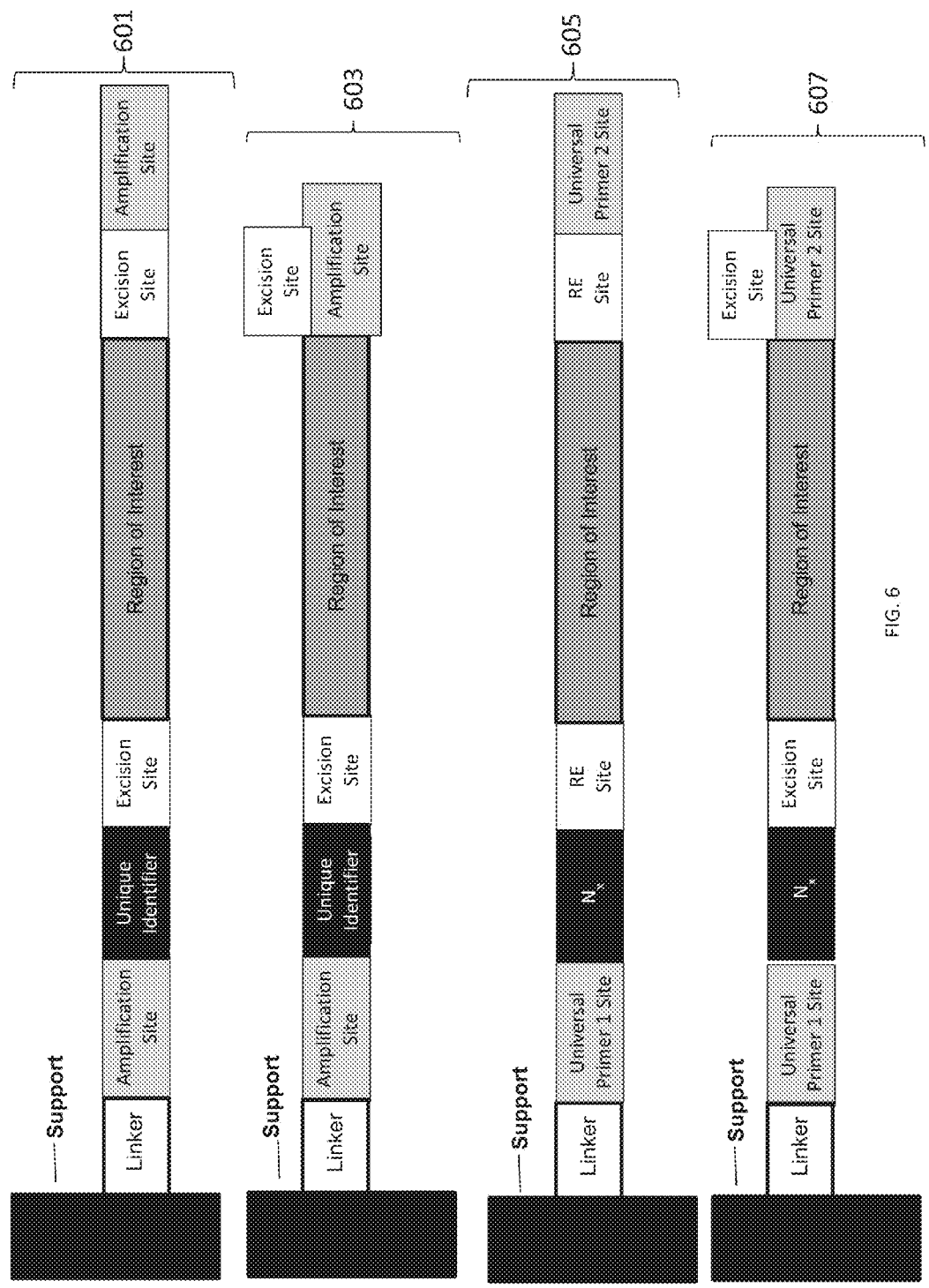
FIG. 6 is a schematic diagram showing exemplary constructs comprising four potential amplification sites and two excision sites for use in a fifth aspect of the invention.

FIG. 6 shows other constructs of the invention (601 through 607) wherein a linker molecule is present between the support and the construct. In one aspect this linker can be used to immobilize the construct to the support. Such a linker can be a nucleic acid sequence, a binding molecule that is used in the attachment of the construct to the substrate, or other structure that can be used to provide desirable attributes to the construct, e.g., to increase the availability of the amplification sites, to provide structural stability to the construct, and the like.

In a specific aspect, the linker molecule also provides a cleavage site for removal of the construct from the substrate. This is useful in instances when it is desirable to remove the construct from the support and keep all other elements of the construct intact. Exemplary linkers include, but are not limited to, polynucleotide linkers and non-nucleotide linkers, such as peptide based linkers or synthetic molecules such as polyethylene glycol.

Figure 7:
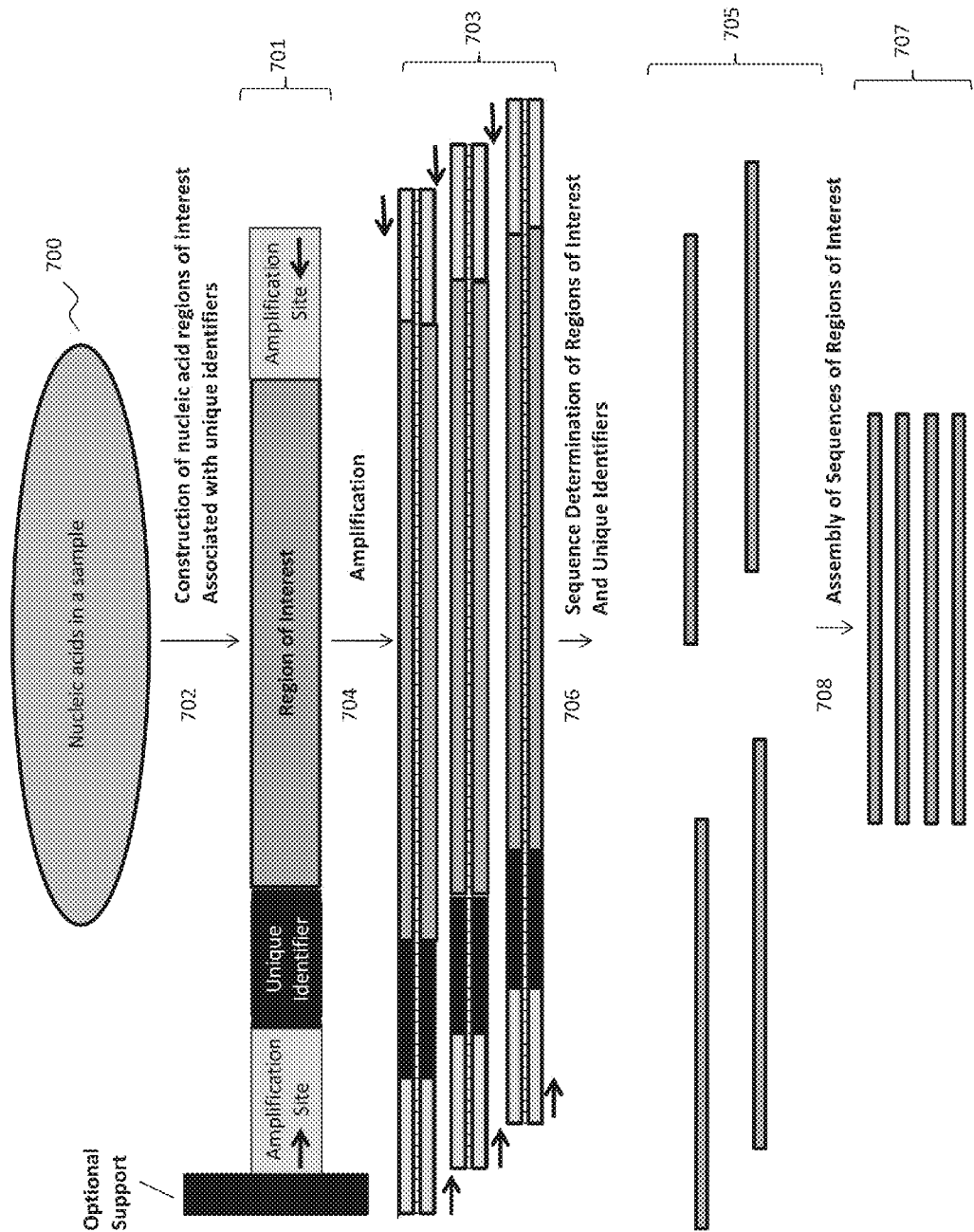
FIG. 7 is a schematic diagram showing one method of nucleic acid determination using the exemplary construct of FIG. 1.

The construct illustrated in FIG. 1, and as also set forth in FIGS. 2-6, can be used for sequence determination and the assembly of consensus sequences using methods such as the one illustrated in FIG. 7. In this method, nucleic acids from a sample (700), are associated 702 with one or more amplification sites and a unique identifier, each in oligonucleotide form to create the constructs shown here at 701. These are amplified 704 to create pools containing identical descendants of each construct 703 containing an ROI and a unique identifier. The sequence is then determined 706 for the pool of amplified constructs 705. These sequences are then optionally assembled 708 to create a consensus sequences 707.

Figure 8:
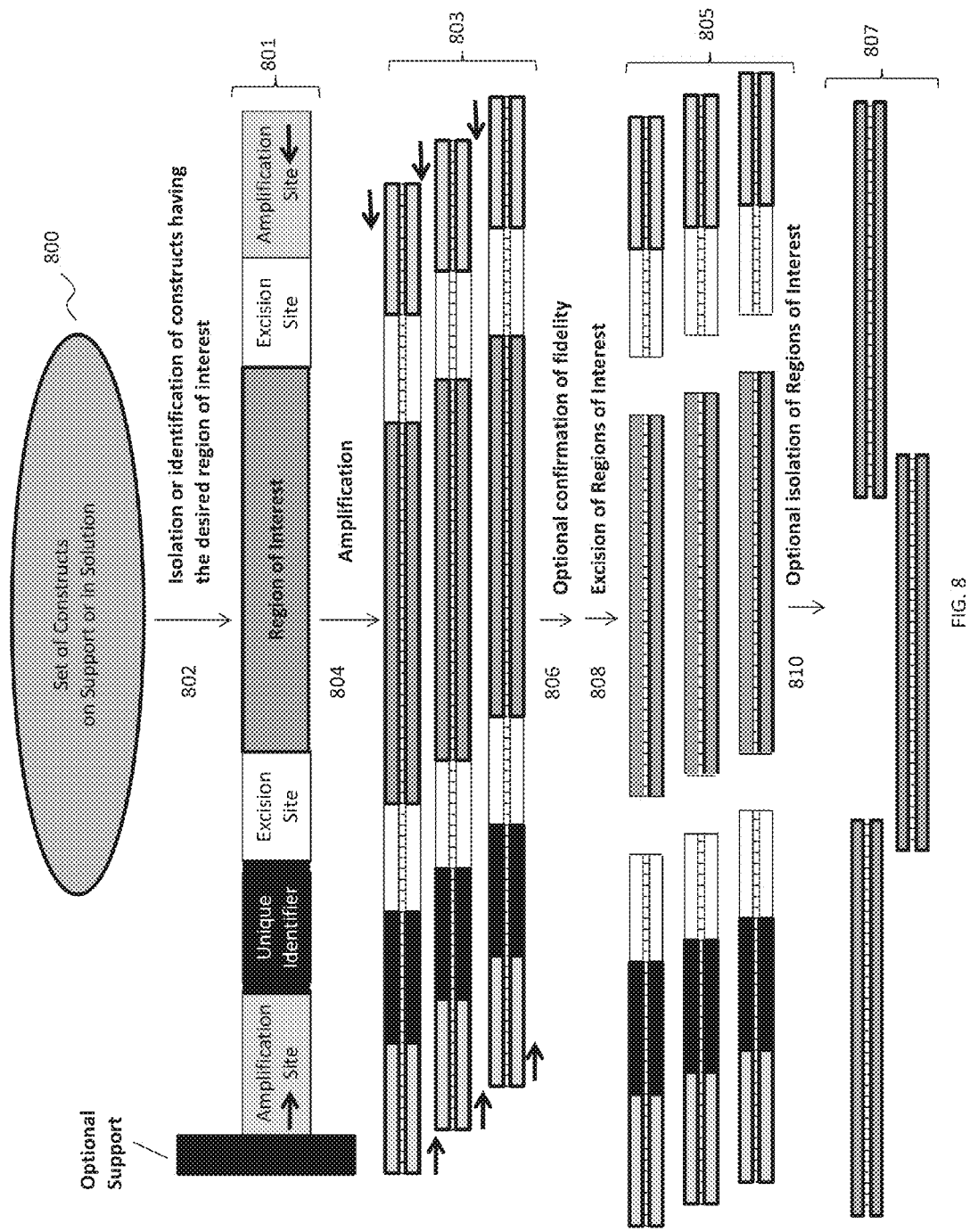
FIG. 8 is a schematic diagram showing one method of nucleic acid selection using the exemplary constructs of FIGS. 2-6.

The constructs illustrated in FIGS. 2-6 can be used for construct selection and/or ROI isolation using methods such as the one illustrated in FIG. 8. In this method, sets of constructs (800), such as those illustrated in FIGS. 2-6 and as shown here at 801, are provided, optionally immobilized to a solid support. Constructs having the desired ROI(s) are selected (802) (e.g., selected for sequence using various sequencing technologies) from the master set. These selected constructs undergo a limited amplification (804), resulting in a small number of identical copies of the selected constructs (803). Following this amplification, the sequence of the construct is optionally confirmed, e.g., by sequencing (806). The ROI is then excised from the construct using the excision sites flanking the ROI region (808), separating the ROIs from the remaining elements of the constructs (805). The ROIs are optionally isolated from the remaining elements of the construct (810) to yield purified ROIs (807).

Figure 9:
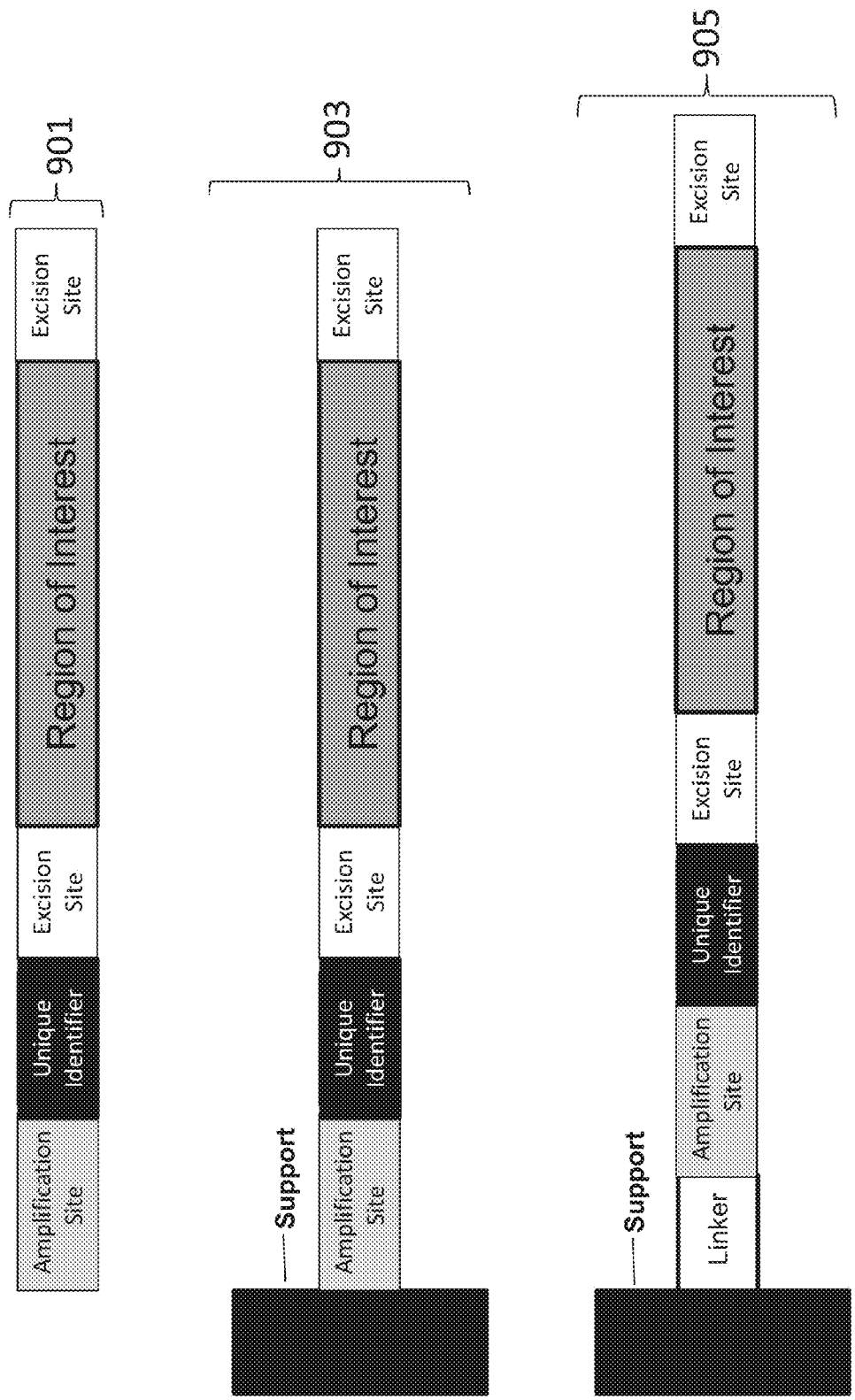
FIG. 9 is a schematic diagram showing exemplary constructs comprising a single amplification site and two excision sites for use in a sixth aspect of the invention.

FIG. 9 illustrates exemplary constructs having one amplification site and two excision sites. The construct may be a free oligonucleotide, as illustrated in FIG. 901, or it may be provided immobilized to a support, with (905) or without (903) a linker molecule.

Figure 10:
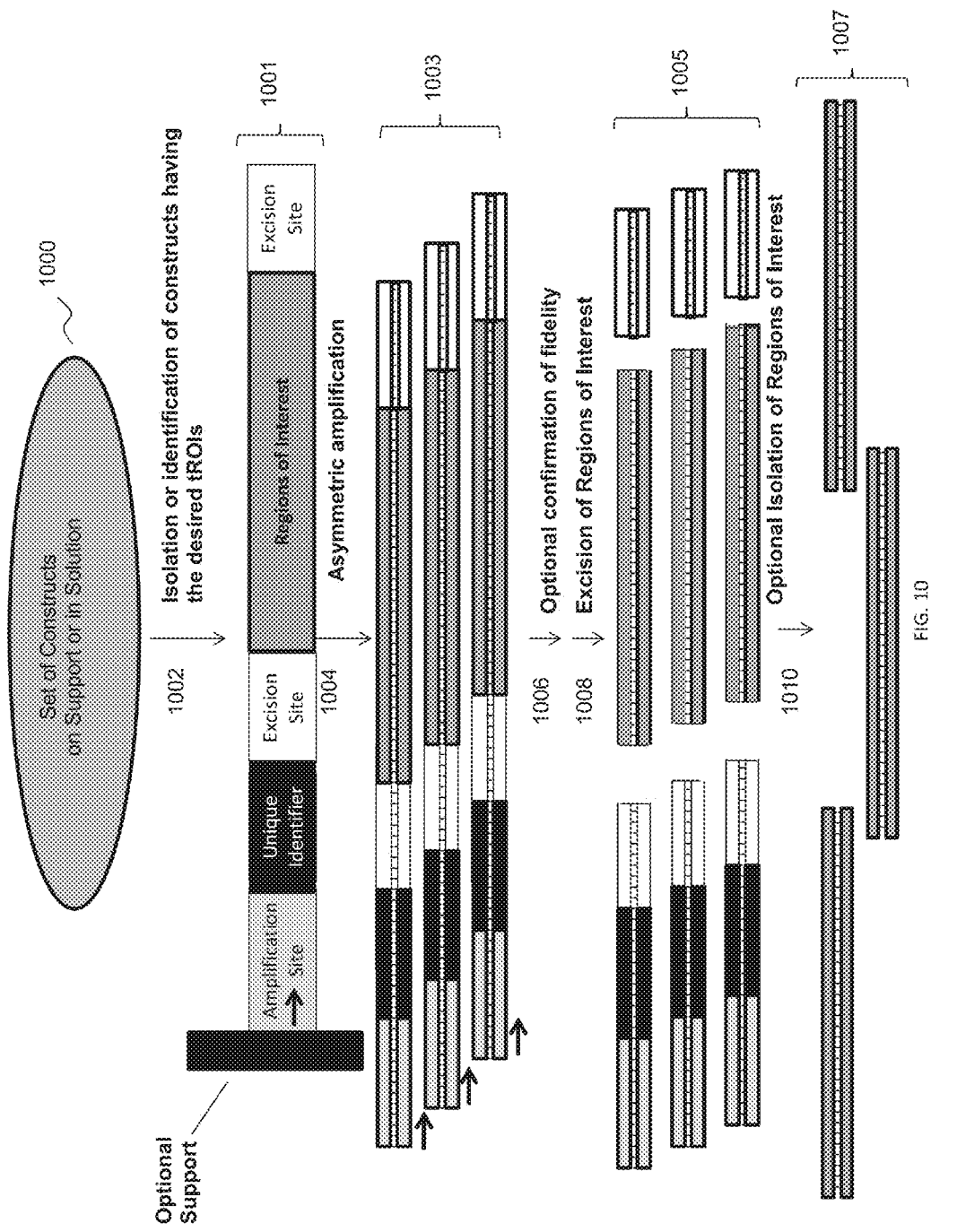
FIG. 10 is a schematic diagram showing one method of selection using the exemplary constructs of FIG. 8.

The constructs illustrated in FIG. 9 can be used for construct selection and/or ROI isolation using methods such as the one illustrated in FIG. 10. In this method, a set of constructs (1000), such as the construct shown here at 1001, are provided, and the constructs are optionally immobilized to a solid support. Constructs having the desired R01(s) are selected (1002) (e.g., selected for sequence using various sequencing technologies) from the master set. These selected constructs undergo a limited asymmetric amplification (1004), resulting in a small number of identical copies of the selected constructs (1003). Following this amplification, the sequence of the construct is optionally confirmed, e.g., by sequencing (1006). The ROI can be excised 1008 from the construct using the excision sites flanking the ROI region, which separates the ROIs from the remaining elements of the constructs (1005). The ROIs are optionally isolated from the remaining elements of the construct (1010) to yield purified ROIs (1007).

Figure 11:
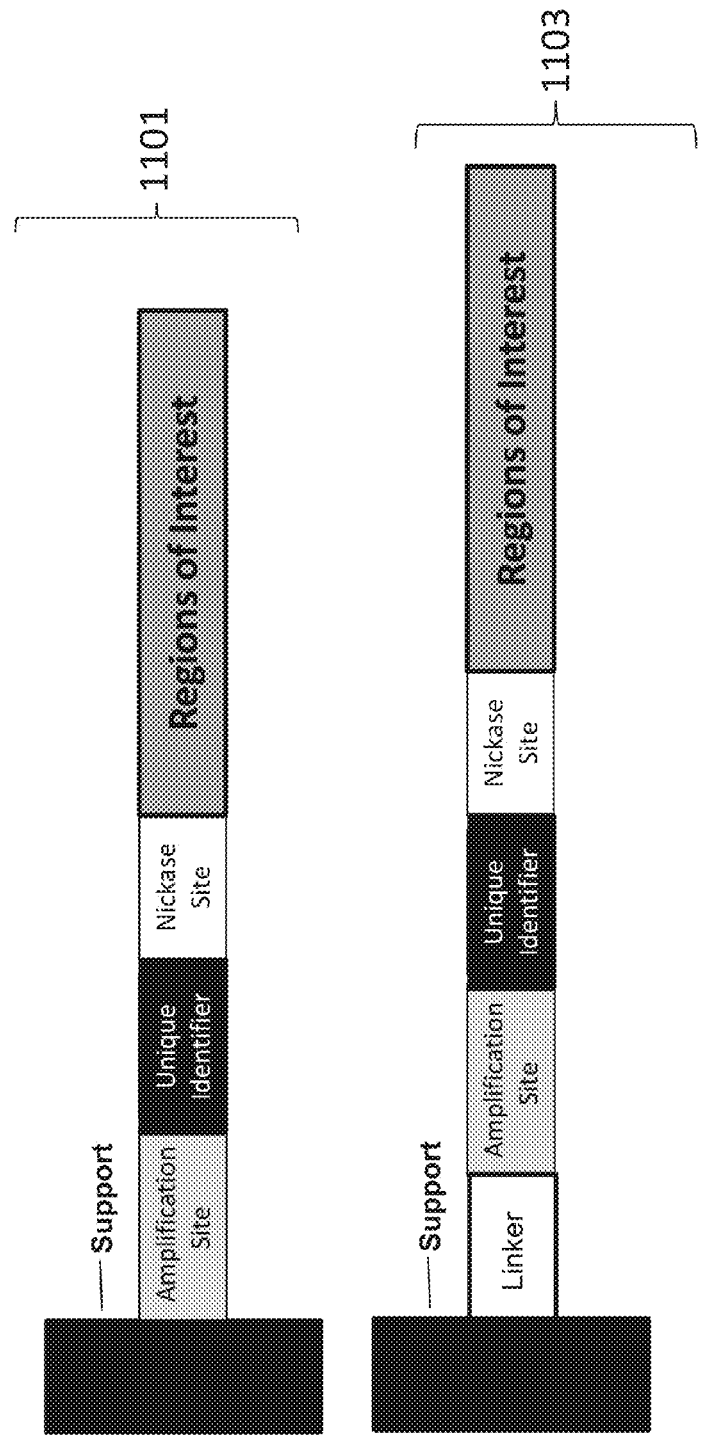
FIG. 11 is a schematic diagram showing exemplary constructs comprising a single amplification site and a single excision sites for use in a seventh aspect of the invention.

FIG. 11 illustrates exemplary constructs having one amplification site and one excision site, in this particular aspect a nickase site for cleavage of one strand of the construct. The constructs are attached to a support to allow excision of the ROI, and may be immobilized on the support with (1103) or without (1101) a linker molecule.

Figure 12:
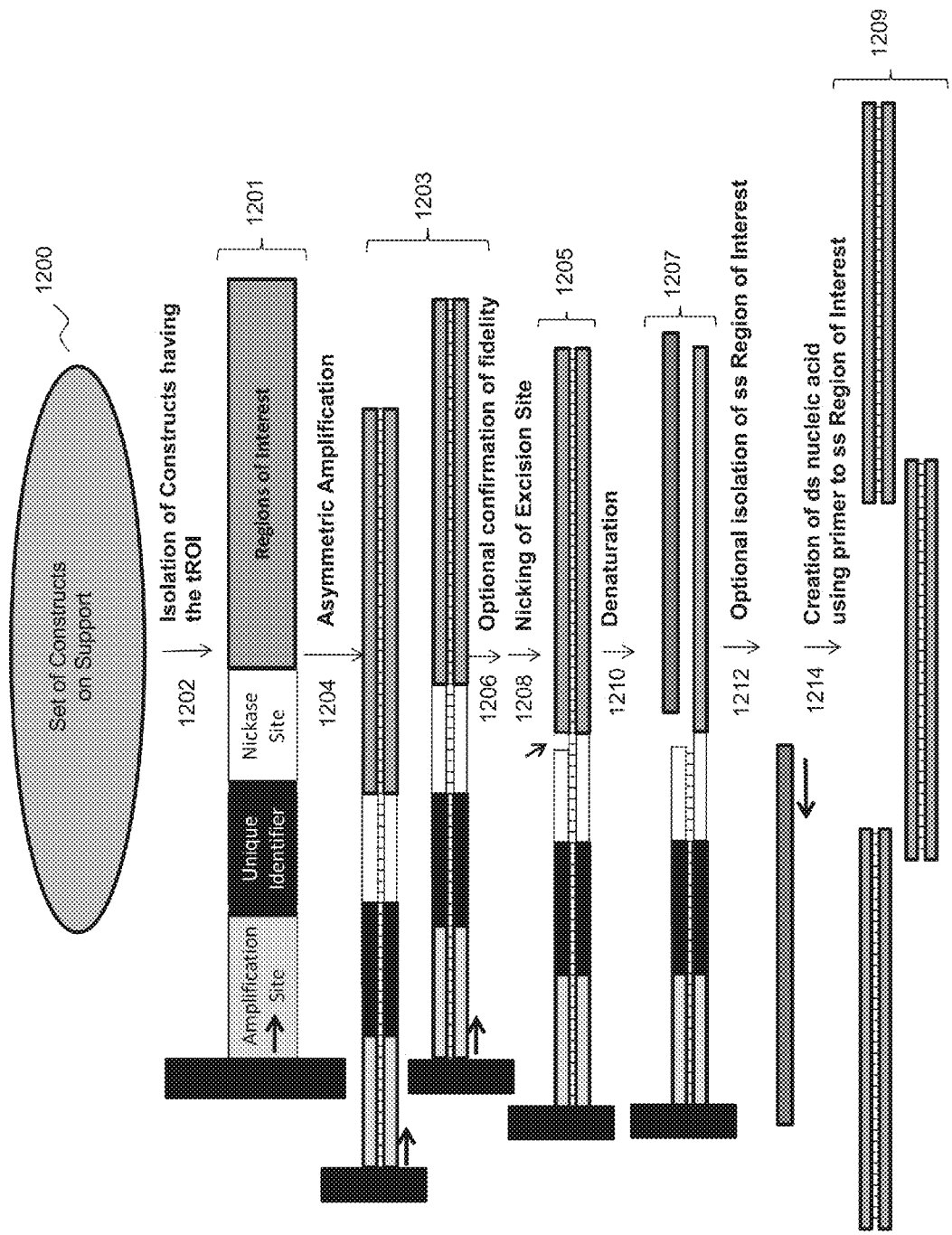
FIG. 12 is a schematic diagram showing one method of selection using the exemplary constructs of FIG. 10.
Figure 13:
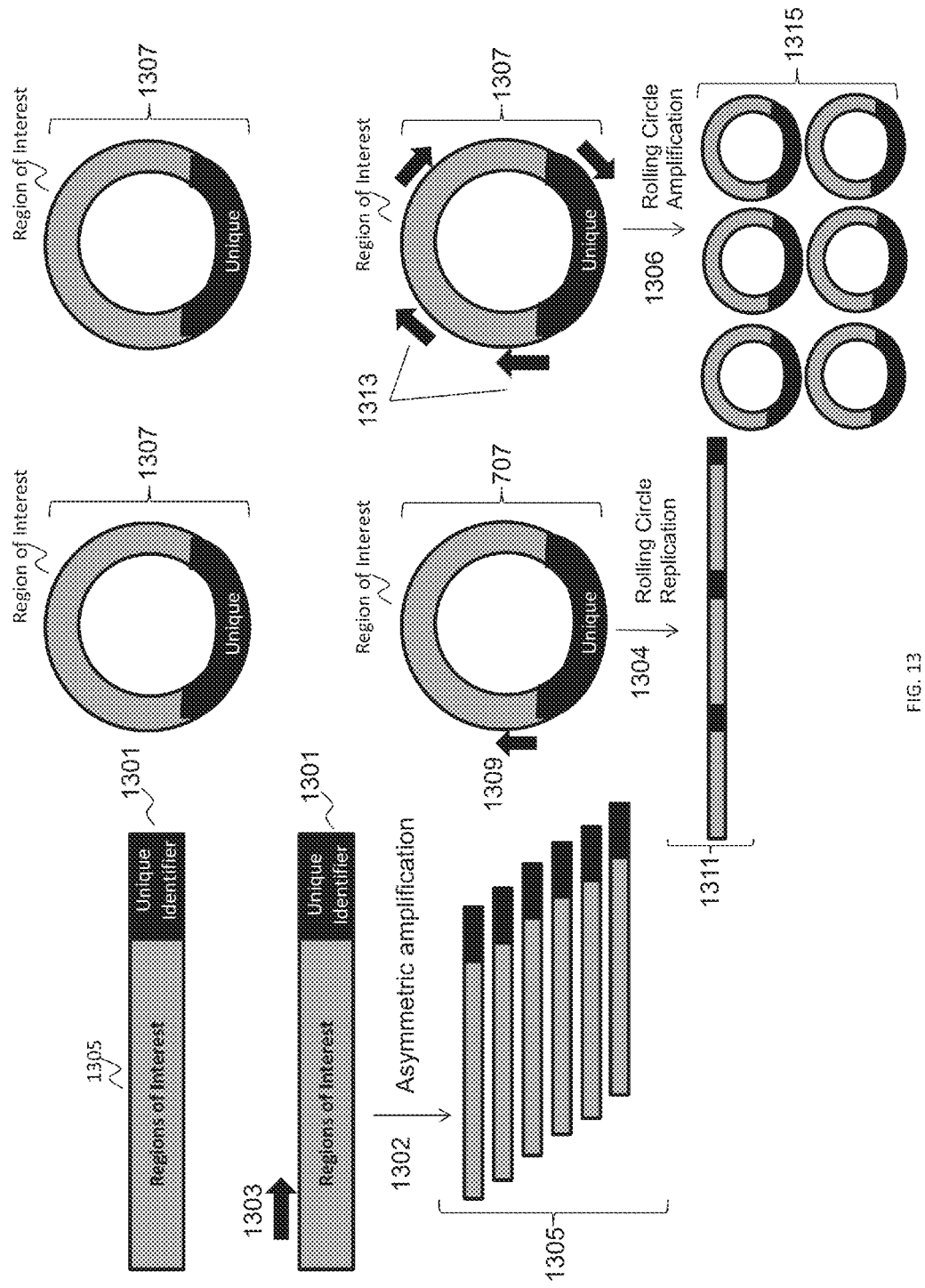
FIG. 13 is a schematic diagram illustrating certain fundamental constructs of the invention and methods of amplifying or replicating these structures.

The constructs illustrated in FIG. 11 can be used for construct selection and/or ROI isolation using methods such as the one illustrated in FIG. 12. As illustrated in FIG. 12, sets of constructs (1200) having the desired ROI(s) are selected (1202) from the master set. These constructs, such as the one shown here at 1201, are attached to a solid support. These selected constructs then undergo a limited asymmetric amplification (1204), resulting in a small number of identical copies of the selected constructs (1203). Following this amplification, the sequence of the construct is optionally confirmed, e.g., by sequencing (1206). The ROI is then excised from the construct by nicking 1208 at the excision site found adjacent to the ROI region, and the strand with the nick is separated 1210 from the immobilized construct, e.g., by denaturation to create a free, ss ROI and remaining elements of the construct attached to the substrate. The ss ROIs are optionally converted (1214) to a ds ROI using a primer that is complementary to the ROI, and the ds ROI optionally isolated (1209).

In certain specific aspects, the constructs of the invention comprise the very basic elements of the invention—regions of interest coupled with unique identifiers. Such constructs can be either linear (1301) or circular (1307), and may comprise additional elements (not shown) in the constructs.

In one aspect, linear construct 1301 can be amplified using a primer specific to the ROI (1303) which, when used for amplification, will amplify not only the ROI but also the unique identifier associated with that particular ROI. In one example, asymmetric amplification (1302) of these constructs results in multiple identical copies of the initial construct (1305).

In another aspect, the constructs of the invention comprise a region of interest and the unique identifier presented in a circular format (1307). An ROI-specific primer (1309) can be used to initiate rolling circle replication (1304) using, e.g., an enzyme such as Phi29. Such replication will result in tandem repeats of the ROI and the unique identifier (1311).

In yet another aspect, the constructs of the invention comprise a region of interest and the unique identifier presented in a circular format (1307). The circular constructs are subject to rolling circle amplification (1306) using random primers (1313), e.g., random hexamers. Use of random primers (1313) for the amplification operation results in the amplification of circular constructs (1315) that comprise the ROIs and unique identifiers.

Construction of Larger Nucleic Acids

There are a wide variety of methods that can be used to assemble oligos into larger constructs, and these can be used to assemble larger nucleic acids using the isolated ROIs obtained from the present methods. Our purpose is not to enumerate them all here, but some examples include PCR with the oligo set; ligation followed by PCR; ligation followed by cloning in a biological vector; assembly by recombination (e.g., in yeast).

By obtaining long, highly pure oligos of desired sequence, it will be possible to assemble relatively long constructs by annealing the oligos together so that hybridization ensures that correct sequences are brought together. Polymerization, ligation, or a combination of both can be carried out. In some aspects, this assembly can occur in a liquid medium. In other aspects, the ROIs obtained from the constructs of the invention are sequentially assembled onto an anchor that is attached to a solid phase.

Such assembly of molecules can then be used to generate large molecular constructs, or a large collection of smaller ones. This can be used to ensure the accuracy of larger synthetic molecules, or to provide a highly validated collection of nucleic acids for use in further analysis.

Improved Quantification of ROIs

Methods to determine the relative amounts of nucleic acids from a sample often require amplification methods in order to have enough material to carry out the desired testing. Conventional methods do not take into account potential areas of technical bias, including bias in amplification of certain sequences. By creating constructs comprising the nucleic acids directly isolated from a sample, bias due to subsequent manipulation of the molecules can be identified by determining the amounts of constructs with unique identifiers. Thus, if a nucleic acid is either over-represented or under-represented due to amplification bias, the number of molecules comprising unique identifiers will also be over-represented or under-represented, and the quantification of the molecules can be corrected to reflect this manner of bias.

Measurement of Error Rates and Local Variances Thereof

In specific aspects, the sets of constructs of the invention can be used to compare amplification rates and/or error rates of different forms or approaches of amplification. This is possible because amplification products can be identified as originating from a single construct, even when constructs have ROIs that are very similar or identical in sequence. Therefore, differences in the amount and/or composition of amplification products can be detected and quantified, and comparisons of these differences can be made between constructs. Comparison can be carried out within a single set, or comparisons can be made between sets, for example pre- and post-amplification, or to a standard, or between two or more empirical forms of amplification. Importantly, the ability to identify the rate of amplification of various, discrete ROIs in the individual constructs provides the ability to monitor and quantify local differences in amplification bias, which allows a more refined assessment of the fidelity of different amplification techniques and enzymes.

In addition to analyzing differences in amplification rate, differences in amplification fidelity can also be analyzed. For example, a polymerase used in an amplification operation may have an overall error rate lower than most other polymerases, but it may display a demonstrably higher rate of error in amplification of specific nucleic acid regions, including but not limited to AT-rich regions, areas of trinucleotide repeats, areas with homopolymer repeats, and the like. The invention allows assessment not only of an overall error rate of an amplification method, but also any fidelity issues based on local variances and/or more specific sources of error.

It can be seen that amplification represents only one type of manipulation of a set. Other types of manipulation are amenable to the same type of analysis. For example, biases in enrichment or depletion of sequences can also be analyzed.

The preceding merely illustrates the principles of the invention. It will be appreciated that those skilled in the art will be able to devise various arrangements which, although not explicitly described or shown herein, embody the principles of the invention and are included within its spirit and scope. Furthermore, all examples and conditional language recited herein are principally intended to aid the reader in understanding the principles of the invention and the concepts contributed by the inventors to furthering the art, and are to be construed as being without limitation to such specifically recited examples and conditions. Moreover, all statements herein reciting principles, aspects, and embodiments of the invention as well as specific examples thereof, are intended to encompass both structural and functional equivalents thereof. Additionally, it is intended that such equivalents include both currently known equivalents and equivalents developed in the future, i.e., any elements developed that perform the same function, regardless of structure. The scope of the present invention, therefore, is not intended to be limited to the exemplary embodiments shown and described herein. Rather, the scope and spirit of present invention is embodied by the appended claims.

What is claimed is:

1. A set of nucleic acid constructs from an individual, wherein
   a) each construct of the set comprises:
      a naturally occurring nucleic acid region of interest (ROI) from the individual;
      at least one unique identifier attached to the ROI that distinguishes the construct from other constructs in the set with a same ROI, wherein the at least one unique identifier is not part of its attached ROI; and
      at least one amplification site; and
   b) the set of constructs comprises: (i) at least two constructs with the same ROI and different unique identifiers, and (ii) two or more different ROIs.

2. The set of claim 1, wherein one or more of the constructs comprise two or more amplification sites flanking the ROI and the unique identifier.

3. The set of claim 1, wherein one or more of the constructs comprise a single amplification site adjacent to the ROI and the unique identifier.

4. The set of claim 1, wherein one or more of the constructs comprise one or more excision sites.

5. The set of claim 4, wherein one or more of the constructs comprise at least two excision sites flanking the ROI.

6. The set of claim 4, wherein one or more of the constructs comprise a single excision site adjacent to the ROI.

7. The set of claim 1, wherein one or more of the constructs are immobilized on a solid support.

8. The set of claim 7, wherein the solid support comprises a bead.

9. The set of claim 1, wherein the set comprises at least five constructs with the same ROI and different unique identifiers.

10. The set of claim 1, wherein the set comprises at least five constructs with the same ROI, different unique identifiers, and at least one excision site.

11. The set of claim 1, wherein one or more of the unique identifiers comprise a degenerate nucleic acid sequence.

12. The set of claim 1, wherein the at least one unique identifier comprises at least 10 nucleotides.

13. The set of claim 1, wherein the ROI comprises DNA.

14. The set of claim 1, wherein the ROI comprises RNA.

15. The set of claim 13, wherein the DNA is genomic DNA.

16. The set of claim 1, wherein one or more of the constructs is double-stranded.

17. The set of claim 1, wherein one or more of the constructs is single-stranded.

18. The set of claim 1, wherein one or more of the constructs comprise at least two unique identifier sequences.

19. The set of claim 2, wherein the two or more amplification sites are different from one another.

20. The set of claim 2, wherein the two or more amplification sites are the same.

21. The set of claim 2, wherein the amplification site that is opposite to the unique identifier with respect to the ROI is separate from an adjacent excision site.

22. The set of claim 2, wherein the amplification site that is opposite to the unique identifier with respect to the ROI comprises an excision site.

23. The set of claim 1, wherein the at least one amplification site comprises a universal priming site.

24. The set of claim 1, wherein the ROI comprises a rare sequence variant, a low-frequency mutation, a minor allelic variant, a polymorphism, a mutation, or a haplotype.

25. The set of claim 1, wherein the unique identifier is from a pre-defined set of sequences.

26. The set of claim 1, wherein the unique identifier is from a degenerate set of sequences.

27. The set of claim 1, wherein at least one construct of the set of constructs is enriched.

28. The set of claim 1, wherein each construct comprises two unique identifier sequences.

29. The set of claim 28, wherein the two unique identifiers are attached to one end of the ROI.

30. A set of nucleic acid constructs from an individual, wherein
   a) each construct of the set comprises:
      a naturally occurring nucleic acid region of interest (ROI) from the individual;
      a unique identifier attached to each end of the ROI, wherein the combination of identifiers on each end of a particular ROI distinguishes the construct from other constructs in the set with a same ROI, wherein the identifiers are not part of its attached ROI; and
      at least one amplification site; and
   b) the set of constructs comprises: (i) at least two constructs with the same ROI and different unique identifiers, and (ii) two or more different ROIs.

* * * * *